United States Patent
Gangavaram et al.

(10) Patent No.: US 9,085,559 B2
(45) Date of Patent: Jul. 21, 2015

(54) TRIAZINE-ARYL-BIS-INDOLES AND PROCESS FOR PREPARATION THEREOF

(75) Inventors: Vasanta Madhava Sharma Gangavaram, Andhra Pradesh (IN); Jhillu Singh Yadav, Andhra Pradesh (ID); Radha Krishna Palakodety, Andhra Pradesh (ID); Arun Bandyopadhyay, West Bengal (IN); Siddhartha Roy, West Bengal (IN); Santu Bandyopadhyay, West Bengal (IN); Rakesh Kamal Johri, Jammu (IN); Subhash Chander Sharma, Jammu (IN); Balaram Ghosh, New Delhi (IN); Mabalirajan Ulaganathan, New Delhi (IN); Sakshi Balwani, New Delhi (IN); Bholanath Paul, Uttar Pradesh (IN); Ashok Kumar Saxena, Uttar Pradesh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 13/321,445

(22) PCT Filed: Dec. 31, 2010

(86) PCT No.: PCT/IB2010/003375
§ 371 (c)(1),
(2), (4) Date: Feb. 6, 2012

(87) PCT Pub. No.: WO2011/092547
PCT Pub. Date: Aug. 4, 2011

(65) Prior Publication Data
US 2012/0283263 A1    Nov. 8, 2012

(30) Foreign Application Priority Data

Jan. 29, 2010 (IN) .............................. 175/DEL/2010

(51) Int. Cl.
C07D 403/14 (2006.01)
C07D 251/50 (2006.01)
C07D 251/52 (2006.01)
A61K 31/53 (2006.01)
A61P 11/06 (2006.01)

(52) U.S. Cl.
CPC .............. C07D 403/14 (2013.01); A61K 31/53 (2013.01); C07D 251/50 (2013.01); C07D 251/52 (2013.01)

(58) Field of Classification Search
CPC .. C07D 403/14; C07D 251/50; C07D 251/52; A61K 31/53
USPC .................................. 544/211, 212; 514/245
See application file for complete search history.

(56) References Cited

U.S. PATENT DOCUMENTS 3,451,802 A    6/1969    Neighbors

OTHER PUBLICATIONS

PCT International Search Report and Written Opinion issued for PCT/IB2010/003375 dated Apr. 26, 2011.
R.M. Desai, et al.; "Simple and Efficient Synthetic Routes to Bioactive S-Triazinyl Dithiocarbamate Derivatives" Medicinal Chemistry Research, vol. 17, No. 8; Feb. 14, 2008.

*Primary Examiner* — Venkataraman Balasubramanian
(74) *Attorney, Agent, or Firm* — Colin P. Cahoon; Celina M. Orr; Carstens & Cahoon, LLP

(57) ABSTRACT

A novel heterocyclic compound belonging to 'triazine-aryl-bis-indoles', useful for the treatment of asthma. The pathway by which this compound inhibits asthma is also demonstrated. The present invention also provides a process for the preparation of above compounds and their derivatives are presented.

11 Claims, 7 Drawing Sheets

TRIAZINE-ARYL-BIS-INDOLES AND PROCESS FOR PREPARATION THEREOF

FIELD OF INVENTION

The present invention relates to triazine-aryl-bis-indoles. The triazine-aryl-bis-indoles of general formula 1 are useful for the treatment of asthma. The compound in the present invention is adapted for the treatment of asthma. This invention also relates to the mechanism of action of the present compound in inhibiting asthma. Unique property of the therapy with IICT-TA67 is inhibition of PDE 4 activity and down regulation of Intercellular Adhesion Molecule type 1 (ICAM-1) and Vascular Cell Adhesion Molecule type 1 (VCAM-1) expression which are crucial in asthma pathogenesis. It also relates to the procedure of synthesis of the above heterocyclic compound.

BACKGROUND AND PRIOR ART DESCRIPTION

Asthma is a non-infectious chronic inflammatory disease of the respiratory system characterized by a reversible airways obstruction. Acute airway obstruction, bronchial hyper-responsiveness and inflammatory state of the bronchial mucosa with increase levels of inflammatory mediators, are the most evident phenomenon which characterizes this pathology. Despite the increase in the prescribed anti-asthmatic treatments, the current trends indicate asthma is set to be the most chronic disease in industrialized countries, affecting mostly the children (15%) than the adults (10%).

In addition to asthma, another most common respiratory disorder is chronic obstructive pulmonary disease (COPD), which embraces several inflammatory pathologies that often co-exist. The WHO predicts COPD (Donnelly, L. E.; Rogers, D. F., Therapy for COPD in the $21^{st}$ century, Drugs, 63, 1973-1998, 2003) will become the third most common cause of death world over by 2020 accounting 8.4 million lives. Although asthma for the last 25 years has been managed moderately with a combined bronchodilator and anti-inflammatory therapies, in contrast, COPD have no effective treatments currently, while the efficacy of the corticosteroids is controversial. Moreover chronic use of various anti-inflammatory drugs leads to adverse side effects. Hence, there is an urgent need to develop novel anti-inflammatory drugs having both the bronchodilatory and anti-inflammatory activity, having application to treat both COPD as well as asthma. Thus, the development of therapies for bronchial asthma has become the major focus of the pharmaceutical industry in the field of respiratory disorders.

Design and development of novel PDE-4 inhibitors (Yeoung, K,-P; Drug Discovery Today 14, 812-813, 2009; Houslay, M. D.; Schafer, P.; Zhang, K,Y, J. Drug Discovery Today 10, 1503-1519, 2005; Dal Piaz, V.; Giovannoni, M. P., Eur. J. Med. Chem., 35, 463-480, 2000; Giembycz, M. A. Monaldi Arch Chest Dis. 57, 48-64, 2002; Molfino, N. A., Respiration 72, 105-112, 2005; Conti, M.; Beavo, J. Annu. Rev. Biochem., 76, 481-511, 2007) in therapeutic applications have gained importance from the early 1990s. PDEs are a large family of enzymes that metabolise the second messenger cAMP/cGMP into inactive acyclic systems. The role of cAMP as a second messenger is well established and it modulates the response of immune cells to a variety of stimuli. Elevation of cAMP has generally been associated with inhibition of lymphocyte activity. The elevation of cAMP levels leads to the suppression of the synthesis and release of pro-inflammatory signals, cytokines and inhibit the production of reactive oxygen species.

The PD enzymes are a large family with eleven sub-families. Of these, the PDE-4, 7 and 8 are associated with the metabolism of cAMP. PDE-4 has four distinct genes, PDE-4A, PDE-4B, PDE-4C and PDE-4D (Muller, T.; Engels, P.; Fozard, J. R. Trends Pharmacol. Sci., 17, 294-298, 1996) with specificity to cAMP and thus have become potential therapeutic targets and most of the research is centred around PDE-4 inhibitors. The potential for selective PDE inhibitors to be used as therapeutic agents was predicted earlier (Teixeira, M. M.; Gristwood, R. W.; Cooper, N.; Hellewell, P. G. PDE-4 inhibitors: Trends Pharmacol. Sci., 18, 164-170, 1997). PDE-4 is the selective PD enzyme that metabolises the cAMP. Hence, PDE-4 inhibitors prevent the inactivation of cAMP.

Mesembrine, a major alkaloid present in Selectium torouosum, has been shown to act as a PDE-4 inhibitor (Smith, M.; Crouch, N.; Gericke, N.; Hirst, M. Psychoactive constituents of the genus Sceletium N.E.Br. and other Mesembryanthemaceae: review. J. Ethnopharmacol 50, 119-30, 1996; Pharmaceutical compositions containing mesembrine and related compounds. U.S. Pat. No. 6,288,104). This is the first catechol based natural product that showed PDE-4 activity. Theophylline is the oldest and shows a weak and non-specific PDE inhibition. The most popular and quite potential PDE-4 inhibitor, since its discovery, is rolipram (Griswold, D. E.; Webb, E. F.; Breton, J.; White, J. R.; Marshall, P. J.; Torphy, T. J., Effect of selective phosphodiesterase type IV inhibitor, rolipram, on fluid and cellular phases of inflammatory response, Inflammation 17, 333-44, 1993; Schneider, H. H.; Schmiechen, R.; Brezniski, M.; Seidler, J.; Eur. J. Pharmocol., 127, 105-115, 1986), a catechol based compound and structurally related to mesembrine. Rolipram, thus has become a template for the synthesis of novel inhibitors, besides becoming a reference drug in evaluating other inhibitors. Ariflo (cilomilast, SB-207,499; Profita, M, Chiappara G, Mirabella, F Chimenti, G Di, L, Costanzo, G, Riccobono, L Bellia V, Bousquet J, and Vignola A. Effect of cilomilast (Ariflo) on TNF-, IL-8 and GM-CSF release by airway cells of patients with COPD. 58, 573-579, 2003. Ochiai, H.; Ohtani, T.; Ishida, A.; Kusumi, K.; Kato, M.; Kohno, H.; Kishikawa, K.; Obata, T.; Nakai, H.; Toda, M. Bioorg. Med. Chem. Lett., 14, 207-10, 2004), roflumilast (Hatzelmann, A.; Schudt, C. J. Pharmacol. Exp. Ther. 297, 267-290, 2001), CDP-840, HT-0712, filaminast are some of the rolipram related active PDE-4 molecules, while V-11294A which is in phase-II clinical trials represents a hybrid molecule of xanthine and rolipram. Cilomilast, roflumilast, BAY-19-8004 and arofylline are in phase-III clinical trials.

The most common and worrisome aspect in the development of potent PDE-4 inhibitors is their propensity for side effects such as nausea and vomiting. The mechanism by which the PDE-4 inhibitors induce side effects are uncertain. However, the family of PDE-4 enzymes exist in two different conformational states (Souness, J. E.; Rao, S. Cell Signal, 9, 227-236, 1997; Duplantier, A. J. et al., J. Med. Chem. 39, 120-125, 1996), distinguishable with their affinity towards rolipram: the conformation with low affinity for rolipram is LAR conformation (PDE-4L), while the one with high affinity is known as HAR conformation (PDE-4H). PDE-4L is associated with anti-inflammatory activity, while the PDE-4H conformation correlates with adverse effects such as emsesis. Thus, there is till an urgent need for the development of promising PDE-4 inhibitors (a) related to rolipram structure or (b) structurally different class of compounds.

Rolipram, with the perspective of medicinal chemistry is a simple catechol derivate, resembling the alkaloid mesembrine. It has two pharmacophores: (a) 3,4-dialkoxy phenyl ring and (b) pyrrolidine-2-one. Though rolipram has disadvantages of the side effects, it has worked as an excellent model for the potent molecules like cilomilast/roflumilast (Phase-III) and others.

In the present invention it was thus desirable to prepare New Chemical Entities (NCEs) to realize the desirable features as a potent PDE-4 inhibitor. In the development of novel molecules it is anticipated to overcome the problems such as emesis, gastric acid secretion associated with rolipram, besides, aiming to dissociate catalytic site inhibition and binding site affinity. Therefore in the present work, development of selective and novel PDE-4 inhibitors was based on: (a) simple chemistry, (b) PDE-4 selectivity and (c) in vtrolin vivo strong potency.

Indoles, bis-indoles and octahydro indoles are part structures of several biologically active compounds (Higuchi, K.; Kawasaki, T. *Nat. Pro. Rep.* 24, 843-868, 2007; O'Connor, S. E.; Maresh, J. *Nat. Pro. Rep.* 23, 532-547, 2006). Indole ring system is a very important component in many synthetic pharmaceuticals (Olgen, S.; Kaessler, K.; Nebioglu, D.; Joachim, J. *Chem. Biol. Drug Des.*, 70, 547-551, 2007; Smart, B. P.; Oslund, R. S.; Walsh, L. A.; Gelb, M. N. *J. Med. Chem.*, 49, 2858-2860, 2006), while the World Drug Index contains 74 indole derivatives as drug molecules. Octahydro indole is part structure of mesembrine, an alkaloid with PDE-4 inhibitory activity. Furthermore, the indole 3-acetic acid and its derivatives have found use as building blocks for the synthesis of pharmaceutically important molecules (Hopkins, C. R. et al., *Bioorg. Med. Chem. Lett.*, 15, 2734-2737, 2005) while, AWD-12-281, (PDE-4 active compound with lower emetic effects), which is in phase-III clinical trials, is an indoleglyoxamide derivative (Kuss, H.; Hoefgen, N.; Johanssen, S.; Kronbach, T.; Rundfeldt, C. *J. Pharmacol. Exp. Ther.* 307, 373-385, 2003). Likewise, the 1,3,5-triazine skeleton is implicated in a variety of therapeutic activities and some triazine derivates have shown anti-asthmatic activity (Leroux, F.; van keulen, B. J.; Daliers, J.; Pommery, N.; Henichart, J. P. *Bioorg. Med. Chem. Lett.*, 7, 509-516,1999).

Thus, the present invention deals with the synthesis of NCEs based on novel 'triazine-aryl-bis-indole' skeleton (See for bis-indole based natural products: Ravikanth, V.; Imelda, O.; Wagner-Döbler, I.; Laatsch, H. *J. Nat. Pro.* 66, 1520-1523, 2003).

The thus prepared NCEs of the present invention are envisaged to address the problems associated with the earlier PDE-4 inhibitors and will have better and improved therapeutic indices. The present invention thus reports the synthesis of novel class of new 'triazine-aryl-bis-indoles', hybrid structures of substituted triazine, indoles and catechol in this patent, wherein, the new class of novel compounds differ with rolipram structurally: (a) the pyrrolidine ring system is replaced with a bis-indolyl acetic acid moiety and (b) the cyclopentyl group is replaced with a substituted triazinyl unit.

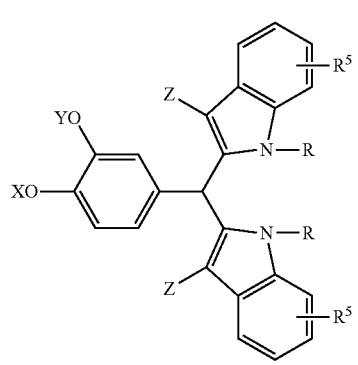

Formula I

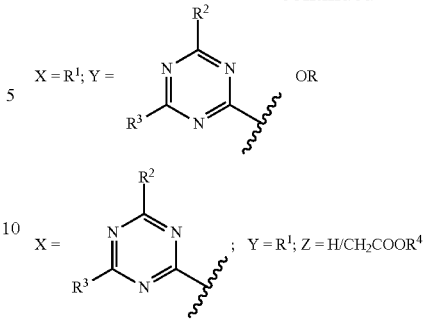

These structurally novel NCEs are envisaged as potential PDE-4 inhibitors devoid of the side effects. The suggested modifications in delineating a hybrid structure of Formula I is not obvious and lot of effort has gone in the designing of such a skeleton as represented in Formula I. The synthesis of the novel 'triazine-aryl-bis-indole' derivatives is reported for the first time in this patent. Likewise, the biological activity of the above NCEs is reported for the first time in this invention. The rationale in the design of the present invention for the synthesis of 'triazine-aryl-bis-indoles' are: (a) octahydroindole, indole and indole acetic acid are part structures of several pharmaceutically important compounds, besides, some anti-asthma compounds, (b) the triazines are also implicated in anti-asthma activity and (c) the catechol derived earlier compounds have shown reasonable PDE-4 activity. Hence, the hybrid structure proposed in the present invention is envisaged to show potent PDE-4 activity, devoid of the problems associated with earlier rolipram analogues, since the cyclopentyl moiety is replaced with hitherto unusal 1,3,5-trisubstituted triazinyl moiety.

Disclosure involves in vitro data showing PDE 4 inhibition by compound 7, IICT-TA67 molecule (FIG. 1, Table 1) as shown in FIG. 2. Disclosure also involves the in vivo data demonstrating the inhibition of airway hypersensitivity as an indicator of asthma as shown in FIG. 5. It further demonstrates the pharmacokinetics and bioavailability of this molecule in vivo as shown in Table 2.

OBJECTIVES OF THE INVENTION

In one aspect, the present invention is directed towards synthesis of novel PDE 4 inhibitor therapeutically effective for the treatment of asthma and asthma related respiratory diseases.

In other aspect the objective of the present invention is the synthesis of novel 'triazine-aryl-bis-indole' class of compounds with higher therapeutic value to the active compounds.

Another objective in the present invention is to design and synthesize novel class of 'triazine-aryl-bis-indoles' and their derivatives to overcome the problems such as emesis and vomiting associated with the known active compounds.

Yet another objective of the present invention on the synthesis of novel 'triazine-aryl-bis-indoles' and their derivatives and their evaluation is to have more therapeutic accessibility to the compounds presented in the invention.

It is also an objective of the present invention that the novel 'triazine-aryl-bis-indoles' and their analogues will have specific PDE-4 binding capacity devoid of emetic properties.

In yet another objective of the present invention on the novel 'triazine-aryl-bis-indole' class of compounds to express more than one therapeutic activity towards asthma treatment.

Still, another objective of the invention is to provide novel process routes for the synthesis of said novel 'triazine-aryl-bis-indoles' that exhibit significant anti-asthma activity.

Yet another objective of the present invention is to provide novel process routes to the new class of 'triazine-aryl-bis-indoles' using commercially available reagent and shorter chemical sequence.

In yet another objective of the invention is to provide green chemistry routes and catalytic synthetic steps for the large-scale manufacture of the said novel 'triazine-aryl-bis-indole' derivatives.

A further object of the invention is to provide the said novel 'triazine-aryl-bis-indoles', which are totally synthetic, in sufficient quantities for biological evaluation under environmentally friendly process chemical routes.

Yet another objective of the present invention is to find out non-toxic PDE-4 inhibitor which might be useful for the treatment of asthma.

A further objective of the invention is to inhibit the signalling pathway such as expression of intercellular cell adhesion molecule and vascular cell adhesion Intercellular Adhesion Molecule type 1 (ICAM-1) and Vascular Cell Adhesion Molecule type 1(VCAM-1) which is crucial for asthma pathogenesis.

A further objective of the present invention is to find out the compound that inhibit asthma in vivo.

SUMMARY OF THE INVENTION

Accordingly the present invention provides triazine-aryl-bis-indoles of general formula I.

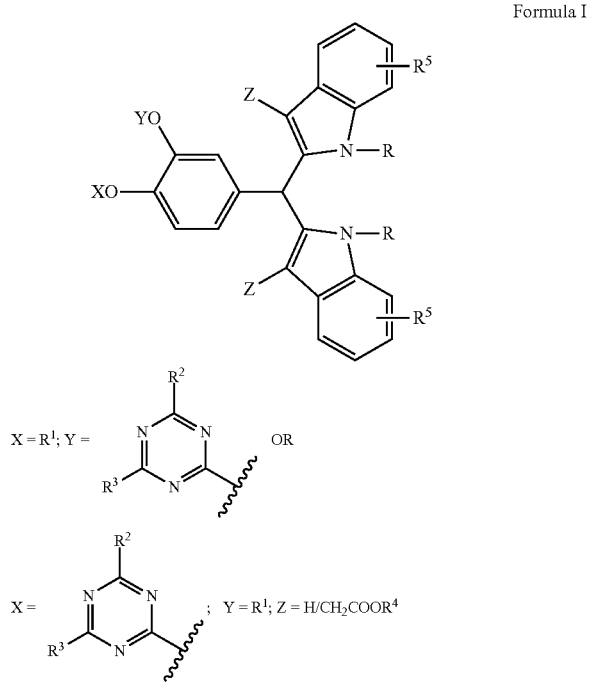

Formula I

Wherein,
R is H, alkyl (C1 to C10) optionally substituted, alkenyl optionally substituted with one or more double bonds, alkynes (C3 to C10) optionally substituted with one or more triple bonds, cycloalkyl (C3 to C7) optionally substituted, aryl, aralkyl, heteroaryl, heteroarylalkyl, C1 to C6 alkyl chain with terminally functionalized such as hydroxyl alkyl (C1 to C6) groups, thio or thioalkyl (C1 to C6) groups, amines, amine salts, mono alkyl amines (C1 to C6 alkyl and C3 to C6 cycloalkyl) groups, α- or β-amino acid moieties, carbohydrate moieties in furanose or pyranose forms, acid amides with aliphatic acids, urethanes with aryl, tert.-butyl or allyl side chains, ureas with aliphatic or aromatic side chains;

$R^1$ is alkyl groups such as methyl, ethyl, n-propyl, C1 to C10 substituted or unsubstituted alkyl groups, substituted with halogens, hydroxyl groups, thio groups, amine, substituted hydroxy, thio and amine groups, cyclic alkyl groups as cyclopropoyl, cyclobutyl, cyclopentyl, cyclohexyl and not limited to the above, optionally substituted cycloalkyl groups with alkyl, halogens, haloalkyl, amine, aminoalkyls;

$R^2$ and $R^3$ are independently alkyl groups such as methyl, ethyl, propyl, and C1 to C10, optionally substituted, aryl groups and heteroaryl groups optionally substituted, aminoalkyl groups substituted optionally with C1 to C10 alkyl groups, amino cycloalkyl groups optionally substituted with C3 to C7, amino carbcocyles C3-C10 substituted optionally, amino aryl groups substituted or unsubstituted, amino heteroaryl groups substituted or unsubstituted, amino hetero-aryl alkyl groups optionally substituted, aminoalkyl groups C1 to C10 substituted terminally or internally with hydroxy groups, hydroxy alkyl groups, hydroxyl aryl groups, hydroxy hetero-aryl groups, amino alkyl groups, dialkylated amino groups, thio or thio alkyl groups, symmetrically dialkylated amino groups with C1 to C10 alkyls optionally substituted, unsymmetrically dialkylated amino groups with C1 to C10 alkyls optionally substituted, substituted diaryl or di hetero-aryl amino groups optionally substituted, symmetrically or unsymmetrically disubstituted diaryl alkyl or di hetero-aryl alkyl amino groups optionally substituted, sugars and amino sugars in furanose form and pyranose form, disaccharides, α-amino acids, linear peptides of α-amino acids, β-amino acids, lower peptides of β-amino acids; Z is H, $CH_2COR^4$, wherein, $R^4$ is O-alkyl, wherein, the alkyl groups are optionally substituted from C1 to C10, O-carbocycles C3 to C7 optionally substituted, O-cycloalkyl groups with one or more spacer groups optionally substituted, O-aryl or aryl alkyl groups substituted optionally, O-hetero-aryl or hetero-aryl alkyl groups substituted optionally, N-alkyl groups C1 to C10 optionally substituted, N-cyclo-alkyl groups C3 to C10 optionally substituted, N-carbocyclic rings optionally substituted, N-aryl or aryl alkyl groups optionally substituted, N-hetero-aryl or hetero-aryl alkyl groups optionally substituted, $R^4$ is amide of α-amino acids, peptides of α-amino acids, β-amino acids, peptides of β-amino acids, amides of amino sugars in furanose form or pyranose form, amides of amino disaccharides;

$R^5$ is a substituent like halogens, such as chlorine, bromine and fluorine, methyl, trifluoromethyl, methoxy, nitro, amino, substituted amino with alkyl groups, aryl and hetero-aryl groups.

In an embodiment of the present invention wherein the structural formula of the representative compounds comprising;

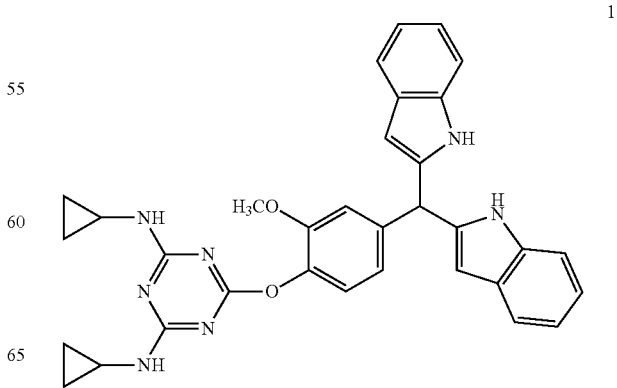

1

2

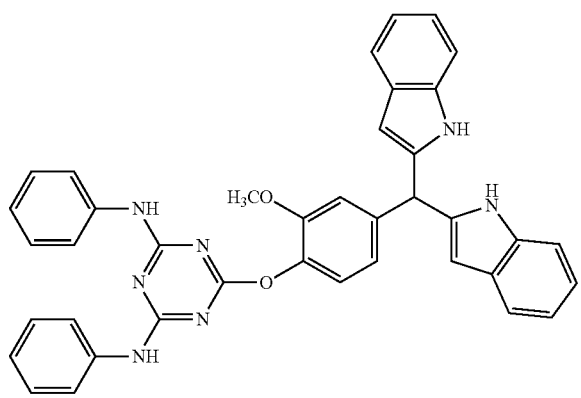

3

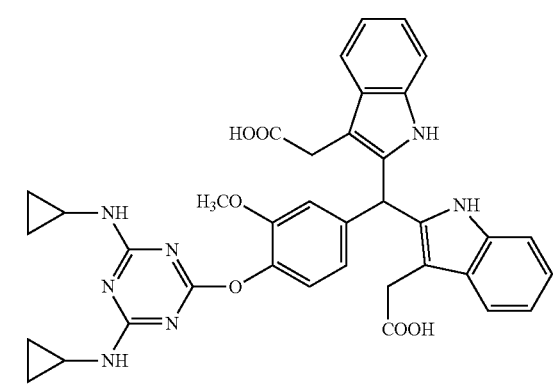

4

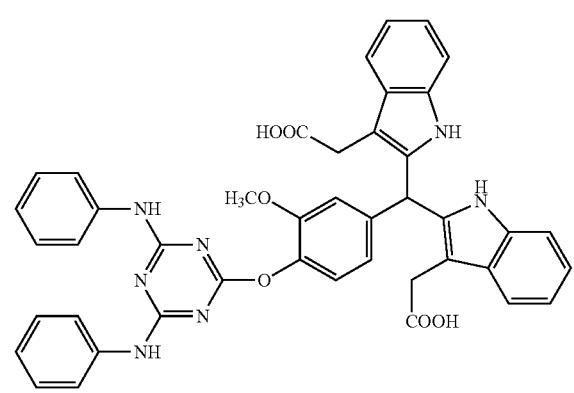

5

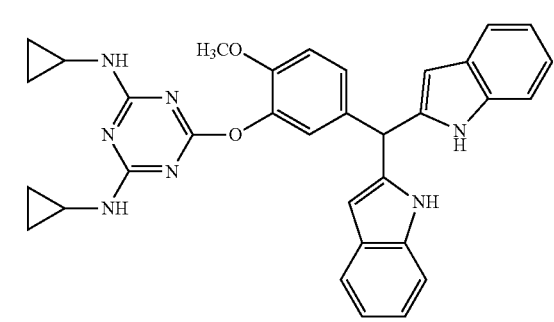

6

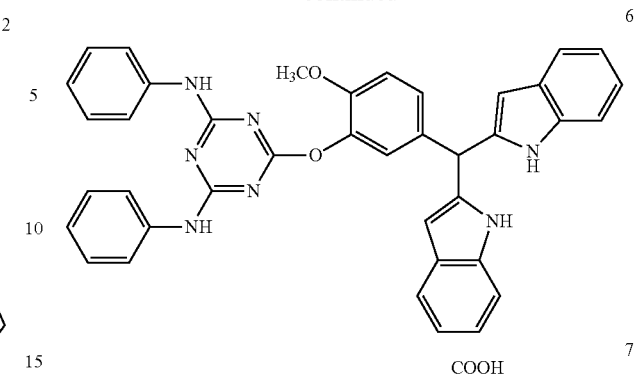

7

8

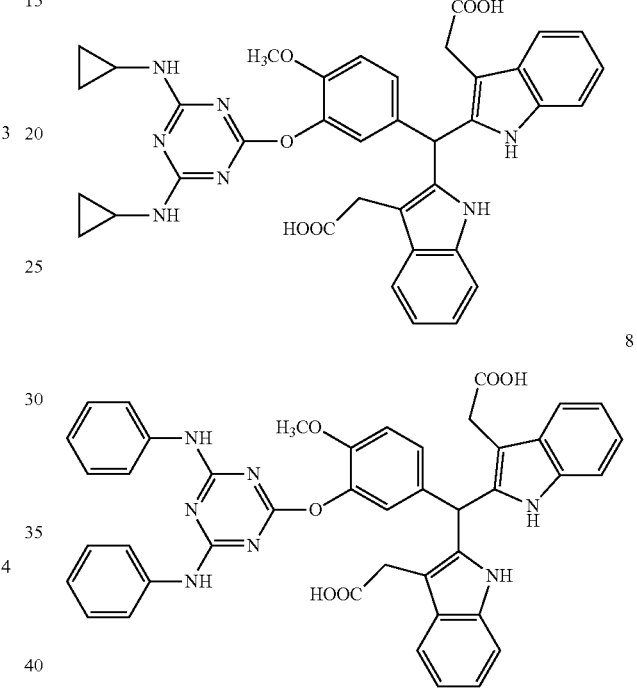

In another embodiment of the present invention wherein the compounds are useful for the treatment of bronchial asthma.

In yet another embodiment of the present invention wherein the compounds inhibit PDE 4 activity in vitro at a dose of 1-20 µg/ml and showed inhibition of PDE-4 enzyme up to 73% taking rolipram as standard.

In a further embodiment of the present invention wherein, wherein the compounds 1-8 at concentrations ranging from 10 µg/mL to 20 µg/mL showed PDE4 inhibition ranging from 16-73%.

In a still embodiment of the present invention wherein, wherein the compounds 10-13 at concentrations ranging from 10 µg/mL to 20 µg/mL showed PDE4 inhibition ranging from 29% to 53%.

In an embodiment of the present invention wherein, wherein the representative compounds comprising:

(i) 2,2'-[2,2'-4-(4,6-bis-cyclopropylamino)-1,3,5-triazin-2-yl-oxy-3-methoxyphenyl]-methylene-bis-1H-indole (1)

(ii) 2,2'-[2,2'-4-(4,6-bis-anilino)-1,3,5-triazin-2-yl-oxy-3-methoxyphenyl]-methylene-bis-1H-indole (2)

(iii) 2,2'-[2,2'-4-(4,6-bis-cyclopropylamino)-1,3,5-triazin-2-yl-oxy-3-methoxyphenyl]-methylene-bis-(1H-indole-3,3-diyl)-diacetic acid (3)

(iv) 2,2'-[2,2'-4-(4,6-bis-anilino)-1,3,5-triazin-2-yl-oxy-3-methoxyphenyl]-methylene-bis-(1H-indole-3,3-diyl)-diacetic acid (4).

(v) 2,2'-[2,2'-3-(4,6-bis-cyclopropylamino)-1,3,5-triazin-2-yl-oxy-4-methoxyphenyl]-methylene-bis-1H-indole (5)

(vi) 2,2'-[2,2'-3-(4,6-bis-anilino)-1,3,5-triazin-2-yl-oxy-4-methoxyphenyl]-methylene-bis-1H-indole (6)

(vii) 2,2'-[2,2'-3-(4,6-bis-cyclopropylamino)-1,3,5-triazin-2-yl-oxy-4-methoxy-phenyl]-methylene-bis-(1H-indole-3,3-diyl)-diacetic acid (7)

(viii) 2,2'-[2,2'-3-(4,6-bis-anilino)-1,3,5-triazin-2-yl-oxy-4-methoxyphenyl]-methylene-bis-(1H-indole-3,3-diyl)-diacetic acid (8)

Accordingly the present invention also provides a process for preparation of triazine-aryl-bis-indole as claimed in claim 1 wherein the process steps comprising;

a) reacting 2,4,6-trichloro-1,3,5-triazine with an amine in presence of a base at a temperature ranging between 0 to 40° C. for a period ranging between 1 to 2 hr to give the disubstituted chloro 1,3,5-triazine of general formula A as shown below:

General formula A

R2/R3 = Aryl or cyclopropyl or alkyl b) reacting the above disubstituted chloro 1,3,5-triazine with aromatic aldehyde in presence of a base at a temperature ranging between 50 to 70° C. for a period ranging between 4 to 6 hr to give the aryl ether of general formula B as shown below:

General formula B

R2/R3 = Aryl or cyclopropyl or alkyl c) reacting the triazine-aryl ethers with indole or indole-3-acetic acid in the presence of an acid at a temperature ranging between 50 to 60° C. for a period ranging between 6 to 8 hr to give triazine-aryl-bis-indole of general formula 1 wherein the R1, R2, R3, R4, R5 as given above:

Formula I $X = R^1; Y =$ OR $X =$ ; $Y = R^1; Z = H/CH_2COOR^4$

In an embodiment of the present invention wherein wherein an amine is selected from an aliphatic amine such as cyclopropyl amine to give 10, or an aromatic amine such as aniline to give 11.

In an embodiment of the present invention wherein, wherein the aromatic aldehydes is selected form vaniline or isovaniline.

The present invention also provides a trisubstituted triazine compound of general formula C wherein R1 is Cl or OX wherein X is General formula C R2 = R3 = cyclopropyl or aryl In an embodiment of the present invention wherein, the representative compounds of general formula C comprising:
1) 4-[4,6-Bis-cyclopropylamino-1,3,5-triazin-2-yl-oxy]-3-methoxy benzaldehyde ($R_2=R_3$=cyclopropyl; 12)
2) 4-[4,6-Bis-anilino-1,3,5-triazin-2-yl-oxy]-3-methoxy benzaldehyde ($R_2=R_3$=phenyl; 13)

3) 4-[4,6-Bis-cyclopropylamino-1,3,5-triazin-2-yl-oxy]-4-methoxy benzaldehyde ($R_2=R_3$=cyclopropyl; 14)

4) 4-[4,6-Bis-anilino-1,3,5-triazin-2-yl-oxy]-4-methoxy benzaldehyde ($R_2=R_3$=phenyl; 15)

The present invention also provides a pharmaceutical composition comprising one or more compounds of general Formula 1 and formula C along with the pharmaceutically acceptable additives, carriers or diluents.

The compounds of general formula 1 and C are useful for the treatment of human bronchial asthma wherein the method comprising administering one or more compounds of formula 1 and formula C by oral, mucosal and any other route to a subject in need for.

Method of treatment of human bronchial asthma with one or more compound of formula 1 according at a dose ranging between of 0.1 to 1 mg/kg BW.

The compound IICT-TA67, which is tested for basal cytotoxicity in 3T3 cells and the $IC_{50}$ found to be 32 mg/L.

The compound IICT-TA67, which is predicted for acute oral toxicity and the predicted acute oral $LD_{50}$ derived to be 430 mg/kg body weight.

DETAILED DESCRIPTION OF THE INVENTION

Figure 1:
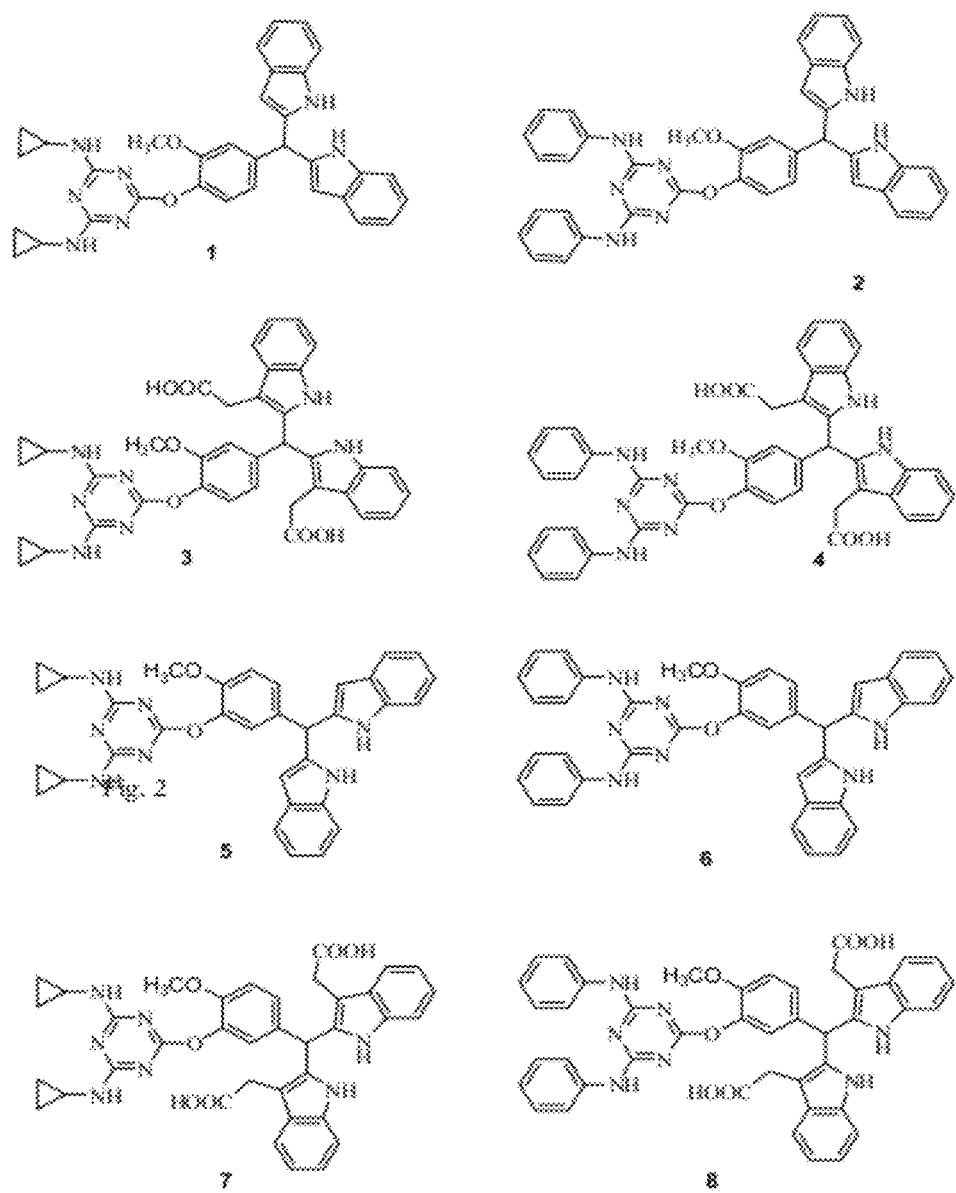
FIG. 1 illustrates the structure of the novel class of triazine-aryl-bis-indole compounds (Compound 1 to 8).

Accordingly, present invention provides a preparation for treating bronchial asthma by inhibiting phosphodiesterase activity with one or more 'triazine-aryl-bis-indole' class of compounds represented by Formula 1.

In particular present invention provides the method of synthesis of diversified 'New Chemical Entities' (NCEs) embedded with a basic skeletal structure consisting of 'triazine-aryl-bis-indoles' frame work.

The present invention also describes that said 'triazine-aryl-bis-indole' compounds and analogous NCEs are potential molecules to inhibit the PDE-4 activity in vitro.

The present invention also describes that said 'triazine-aryl-bis-indole' compounds and analogous NCEs are potential molecules to inhibit the PDE-4 activity towards the treatment of asthma and COPD.

The present invention also describes that said compounds are potential molecules to inhibit the airway hyperresponsiveness towards the treatment of asthma and COPD.

The present invention also describes that said compounds are potential molecules to inhibit TNF-α induced expression intercellular cell adhesion molecule and vascular cell adhesion molecule Intercellular Adhesion Molecule (ICAM) and Vascular Cell Adhesion Molecule (VCAM) activity towards the treatment of asthma and COPD.

It also describes that the said compound 8 is potentially bioavailable with good pharmacokinetics.

It further describes that said compound 8 is potentially non toxic

The present invention describes the synthesis of a novel PDE 4 inhibitor, IICT-TA67 (Compound 7) and its analogues (Compound 1-8) which inhibits asthma in vivo. The same molecule also inhibits expression of cell adhesion molecules such as Intercellular Adhesion Molecule type 1 (ICAM-1) and Vascular Cell Adhesion Molecule type 1(VCAM-1) which plays crucial role in asthma pathway. It further describes the inhibition of adhesion of Neutrophils on TNF-alpha induced HUVECs.

The present invention also describes the method of synthesis of diversified 'New Chemical Entities' (NCEs) embedded with a basic skeletal structure consisting of 'triazine-aryl-bis-indoles' frame work. The said NCEs exhibit excellent activity against phosphodiesterase enzyme (PDE) to become novel PDE-4 specific inhibitors. The novel green chemistry routes developed in the invention are suitable for the synthesis of compounds of the following structural Formula I:

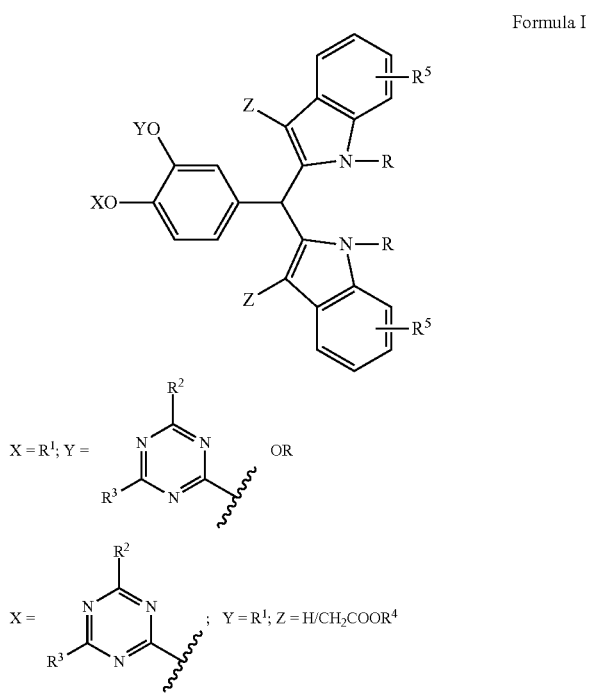

Formula I

R is H, alkyl (C1 to C10) optionally substituted, alkenyl optionally substituted with one or more double bonds, alkynes (C3 to C10) optionally substituted with one or more triple bonds, cycloalkyl (C3 to C7) optionally substituted, aryl, aralkyl, heteroaryl, heteroarylalkyl, C1 to C6 alkyl chain with terminally functionalized such as hydroxyl alkyl (C1 to C6) groups, thio or thioalkyl (C1 to C6) groups, amines, amine salts, mono alkyl amines (C1 to C6 alkyl and C3 to C6 cycloalkyl) groups, α- or β-amino acid moieties, carbohydrate moieties in furanose or pyranose forms, acid amides with aliphatic acids, urethanes with aryl, tert-butyl or allyl side chains, ureas with aliphatic or aromatic side chains $R^1$ is alkyl groups such methyl, ethyl, n-propyl, C1 to C10 substituted or unsubstituted alkyl groups, substituted with halogens, hydroxyl groups, thio groups, amine, substituted hydroxy, thio and amine groups, cyclic alkyl groups as cycloprpoyl, cyclobutyl, cyclopentyl, cyclohexyl and not limited to the above, optionally substituted cycloalkyl groups with alkyl, halogens, haloalkyl, amine, aminoalkyls $R^2$ and $R^3$ are independently alkyl groups such as methyl, ethyl, n-propyl, and C1 to C10, optionally substituted, aryl groups and heteroaryl groups optionally substituted, aminoalkyl groups substituted optionally with C1 to C10 alkyl groups, amino cycloalkyl groups optionally substituted with C3 to C7, amino carbcocyles C3-C10 substituted optionally, amino aryl groups substituted or unsbstituted, amino hetero-aryl groups substituted or unsbstituted, amino hetero-aryl alkyl groups optionally substituted, aminoalkyl groups C1 to C10 substituted terminally or internally with hydroxyl groups, hydroxy alkyl groups, hydroxy aryl groups, hydroxy hetero-aryl groups, amino alkyl groups, dialkylated amino groups, thio or thio-alkyl groups, symmetrically dialkylated amino groups with C1 to C10 alkyls optionally substituted, unsymmetrically dialkylated amino groups with C1 to C10 alkyls optionally substituted, substituted diaryl or di hetero-aryl amino groups optionally substituted, symmetrically or unsymmetrically disubstituted diaryl alkyl or di hetero-aryl alkyl amino groups optionally substituted, sugars and amino sugars in furanose form and pyranose form, disaccharides, α-amino acids, linear peptides of α-amino acids, β-amino acids, lower peptides of β-amino acids Z is H, $CH_2COR^4$, wherein, $R^4$ is O-allkyl, groups optionally substituted from C1 to C10, O-carbocycles C3 to C7 optionally substituted, O-cycloalkyl groups with one or more spacer groups optionally substituted, O-aryl or aryl alkyl groups substituted optionally, O-hetero-aryl or hetero-aryl alkyl groups substituted optionally, N-alkyl groups C1 to C10 optionally substituted, N-cycloalkyl groups C3 to C10 optionally substituted, N-carbo cyclic rings optionally substituted, N-aryl or aryl alkyl groups optionally substituted, N-hetero-aryl or hetero-aryl alkyl groups optionally substituted, $R^4$ is amide of α-amino acids, peptides of α-amino acids, β-amino acids, peptides of β-amino acids, amides of amino sugars in furanose form or pyranose form, amides of amino disaccharides.

$R^5$ is substituents like halogens, such as chlorine, bromine and fluorine, methyl, trifluoromethyl, methoxy, nitro, amino, substituted amino with alkyl groups, aryl and hetero-aryl groups The present invention describes the synthesis and process chemistry for the novel class of compounds such as 'triazine-aryl-bis-indoles' having a catechol derived structure constituting a part of triazine and a part bis-indole moiety on it. The said novel class of compounds are represented by Formula I.

The applicant in the present invention discovered that by the replacement of pyrrolidine-2-one in pharmacophore 'A' of rolipram with bis-indoles and O-cyclopentyl in pharmacophore 'B' with substituted 1,3,5-triazinyl moiety resulting in a novel 'triazine-aryl-bis-indole' hybrid structure represented in Formula I. The said 'triazine-aryl-bis-indole' compounds and analogous NCEs are potential molecules to inhibit the PDE-4 activity towards the treatment of asthma and COPD. The present invention describes the first time synthesis of the said compounds based on 'triazine-aryl-bis-indoles' skeleton and their use in asthma and COPD for the first time. The said compounds of the present invention were found to be potent PDE-4 inhibitors.

DEFINITIONS

The term 'alkyl' refers to a saturated straight chain hydrocarbon of C1 to C10 optionally substituted specifically include methyl, ethyl, n-propyl, iso-propyl, n-butyl, isobutyl, pentyl, hexyl, iso-hexyl, as used herein unless otherwise specified.

The term 'alkenyl' refers to, unless otherwise specified, straight chain hydrocarbon of C3 to C10 with one or more double bonds, optionally substituted.

The term 'carbocycle' refers to, but not limited to, cyclopropyl, cyclobutyl, cyclopentyl, cyclohexyl groups optionally substituted. Similarly, the term 'cycloalkyl' refers to cyclopropyl methyl, cyclobutyl methyl, cyclopentyl methyl, cyclohexyl methyl groups optionally substituted.

The term 'aryl' refers to an aromatic ring while the term 'hetero-aryl' refers to hetero aromatic ring systems with one or more hetero atoms from oxygen, nitrogen, sulphur. The aryl and hetero-aryl groups are substituted optionally with any of the groups selected from but not limited to, consisting of halogens, hydroxyl, amino, alkyl amino, cyano, alkoxy, aryloxy, nitro.

The term 'alkyl aryl' or 'alkyl hetero-aryl' refers to an alkyl group having an aryl or hetero-aryl ring as a substituent, which are optionally substituted with, but not limited to, cyano, nitro, amino, hydroxy, alkoxy, aryloxy, amino alkyl groups.

The term 'monosaccharides' refers to sugars in both the furanose and the pyranose forms, but not limited to hexoses such as glucose, galactose, mannose, pentoses such as xylose, ribose, rhamnose, L-arabinose and D-arabinose, amino sugars. Similarly, the term 'disaccharides' refers to sugars including but not limited to lactose, maltose, others.

The term 'amino acid' refers to α-amino acids including but not limited to with proteinogenic amino acid side chains, non-proteinogenic amino acid side chains and small peptides of the said amino acids.

The term 'β-amino acid' refers to β-amino acids including but not limited to with proteinogenic amino acid side chains, non-proteinogenic amino acid side chains, with protected monosaccharides such as xylose, ribose, arabinose, lyxose in furansoe form, glucose, galactose, mannose in pyranose form.

The present invention further describes novel process for the synthesis of compounds having 'triazine-aryl-bis-indole' skeleton and exhibit potent PDE-4 inhibitory activity. The said process routes described in the present invention utilized commercial reagents, short routes, green chemistry and environmentally friendly reaction conditions. The said process routes are amenable to large scale synthesis of 'triazine-aryl-bis-indoles' in sufficient quantities for further biological evaluation.

In one embodiment the invention describes novel 'triazine-aryl-bis-indole' framework of Formula I, where, R=H, $Y=R^1$=methyl, $X=R^2=R^3$=cyclopropyl amine, Z=H, $R^5$=H.

In another embodiment the invention provides novel 'triazine-aryl-bis-indoles' compounds related to Formula I, where, R=H, $Y=R^1$=methyl, $X=R^2=R^3$=cyclopropyl amine, $Z=CH_2COR^4$ where $R^4$=OH, $R^5$=H.

In yet another embodiment the invention describes novel 'triazine-aryl-bis-indoles' framework of Formula I, where, R=H, $Y=R^1$=methyl, $X=R^2=R^3$=NHPh, Z=H, $R^5$=H.

In another embodiment the invention provides novel 'triazine-aryl-bis-indole' compounds related to Formula I, where, R=H, $Y=R^1$=methyl, $X=R^2=R^3$=NHPh, $Z=CH_2COR^4$ where $R^4$=OH, $R^5$=H.

In still another embodiment the invention describes novel 'triazine-aryl-bis-indole' framework of Formula I, where, R=H, X=R¹=methyl, Y=R²=R³=cyclopropyl amine, Z=H, R⁵=H.

In another embodiment the invention provides novel 'triazine-aryl-bis-indoles' compounds related to Formula I, where, X=R¹=methyl, Y=R²=R³ cyclopropyl amine, Z=CH₂COR⁴ where R⁴=OH, R⁵=H.

In another embodiment the invention describes novel 'triazine-aryl-bis-indoles' framework of Formula I, where, R=H, X=R¹=methyl, Y=R²=R³=NHPh, Z=H, R⁵=H.

In still another embodiment the invention provides novel 'triazine-aryl-bis-indoles' compounds related to Formula I, where, R=H, X=R¹=methyl, Y=R²=R³=NHPh, Z=CH₂COR⁴ where R⁴=OH, R⁵=H.

FIG. 1. The synthesis of 'triazine-aryl-bis-indole' skeletal structures related to Formula I, which are represented by structural formulae 1 to 8 as depicted in FIG. 1. The steps described in the present invention for the process routes for the said novel compounds of formulae 1 to 8 as shown in FIG. 1 are:
(a) reacting trichloro-1,3,5-triazine with appropriate amines such as cyclopropyl amine or aniline
(b) base mediated coupling of substituted 1,3,5-triazine chloride with phenolic groups of vaniline or isovaniline
(c) acid catalyzed condensation of the aldehyde triazinyl ethers with indole or indole acetic acid to provide the NCEs belonging to the novel class of 'triazine-aryl-bis-indoles'

The present invention describes the NCEs as well as pharmaceutical compositions that comprise one or more such compounds. This invention, more specifically describes the novel compounds of formula I, where, R=H, X=R¹=methyl, Y=substituted 1,3,5-triazine with R²=R³=cyclopropyl amine or aniline, Z=H or CH₂COR⁴ where R⁴=OH, R⁵=H.

R=H, Y=R¹=methyl, X=substituted 1,3,5-triazine with R²=R³=cyclopropyl amine or aniline, Z=H or CH₂COR⁴ where R⁴=OH, R⁵=H.

The NCEs prepared in the present invention are used as anti-asthmatic agents specifically as PDE-4 inhibitors. The intermediate compounds that are described in the present invention along with NCEs prepared are useful for other therapeutic applications.

Thus, the present invention as described above provides the first synthetic approach to the synthesis of new and novel class of compounds of 'triazine-aryl-bis-indoles' of general structural formula I as shown, wherein, X, Y, R, R¹, R², R³, R⁴ and R⁵ are as defined earlier.

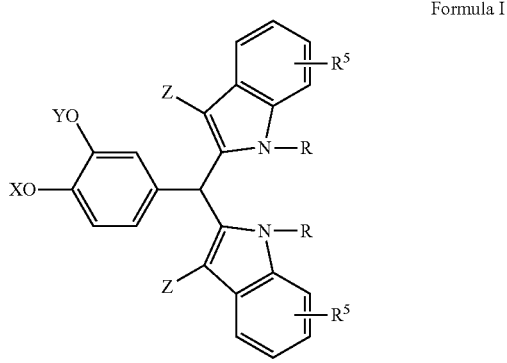

Formula I

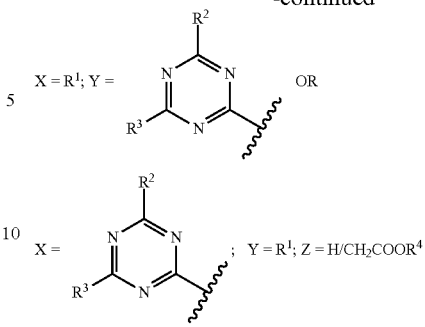

The following schemes I-IV of the present invention exemplify the preparative methods for the particularly preferred compounds. The substitution patterns for the particularly preferred compounds are indicated in the schemes I-IV below. The compounds exemplified in the present invention herein are only representatives for the above class of novel 'triazine-aryl-bis-indole' compounds.

Scheme I in the present invention exemplifies the preferred preparative method for the compounds of structural formula I, compounds of Formulae 1 and 2 as shown in FIG. 1, wherein, R=H, Y=R¹=methyl, X=substituted 1,3,5-triazine with R²=R³ is represented by either cyclopropyl amine or aniline, Z=H, R⁵=H. In this invention cyanuric chloride 9 can be reacted with RNH₂ wherein, R is cyclopropyl or phenyl, in the presence of a base such as sodium hydroxide, potassium hydroxide, potassium carbonate, sodium bicarbonate, cesium carbonate or the like in a solvent such as acetone, ethyl methyl ketone, pentanone, t-butyl methyl ketone, DMF, NMP, dimethyl acetamide or the like, first at low temperature varying from −40 to 5° C. and then at higher temperatures varying from 20-100° C. with another equivalent of RNH₂ to provide the disubstituted triazines 10 (R=cyclopropyl) and 11 (R=phenyl; Sugiura, Y.; Miwatari, S.; Kimura, H.; Knzaki, N. JP 11158073 A2 (Jun. 15, 1999; Takagi, K.; Hattori, T.; Kunisada, H.; Yuki, Y., *Journal of Polymer Science: Part A: Polymer Chemistry*, (2000) 38, 4385-4395), as shown in Scheme I. For the exemplary reaction conditions for 10 wherein R is represented by cyclopropyl, see example 1, part 1, while for 11 wherein R=phenyl, example 2, part 1 (Scheme I).

The chlorides 10 and 11 were independently reacted typically with an aromatic aldehyde like vaniline in a suitable solvent such as acetone, methyl ketone and other ketone solvents or DMF, NMP, dimethyl acetamide or the like in the presence of a base for e.g.: potassium carbonate, sodium hydroxide, potassium hydroxide, sodium hydride, potassium hydride, or the like for a suitable time 4-12 h and temperature varying from 50 100° C. sufficient for reaction to provide the aryl ethers 12 and 13 respectively as shown in Scheme I. See the reaction conditions in example 1, part 2 for 12, and example 2, part 2 for 13 (Scheme I). Compounds of formulae 12 and 13 were independently reacted with indole in the presence of an acid for eg: conc. HCl, aq. HCl solution, HCl gas generated in situ, HCl gas generated in situ from the like of trichlorotriazine (TCT), or Lewis acids like BF₃OEt₄, ZrCl₄, BiCl₃, AlCl₃, InCl₃ or the like in a suitable solvent like CH₂Cl₂, CHCl₃, ethylene dichloride or without a solvent at heating temperature or microwave reaction conditions to provide the compounds 1 and 2 as shown in FIG. 1. The exemplary reaction conditions for the preparation of 1 are shown in example 1, part 3, while the reaction conditions for 2 are presented in example 2, part 3 (Scheme I).

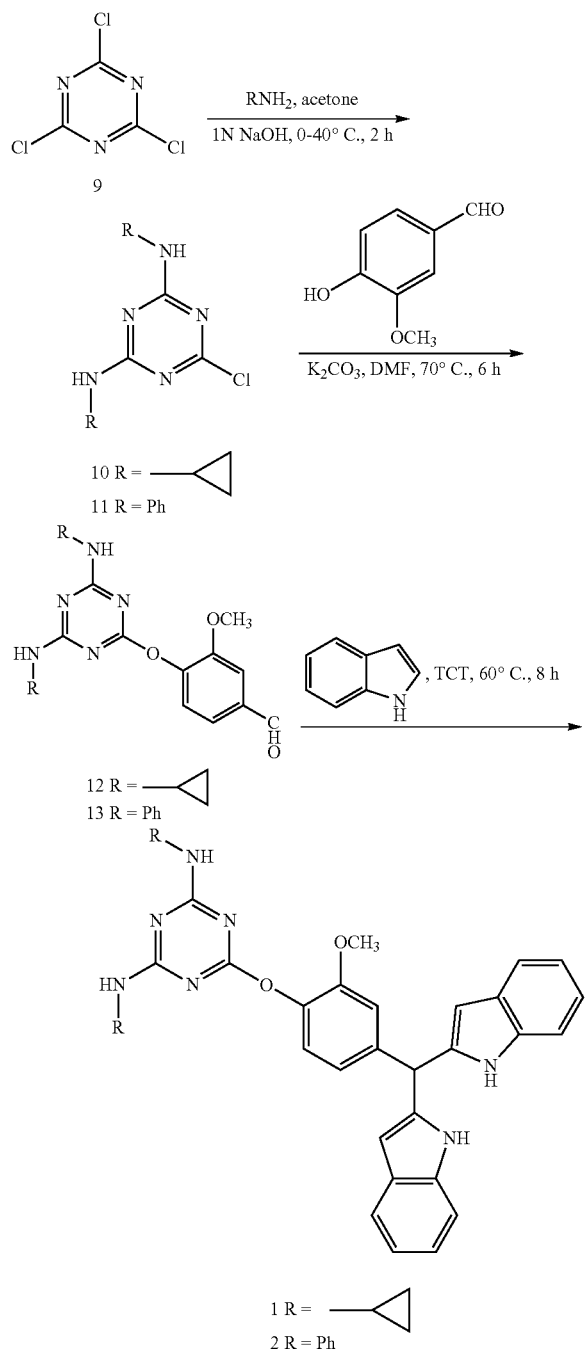

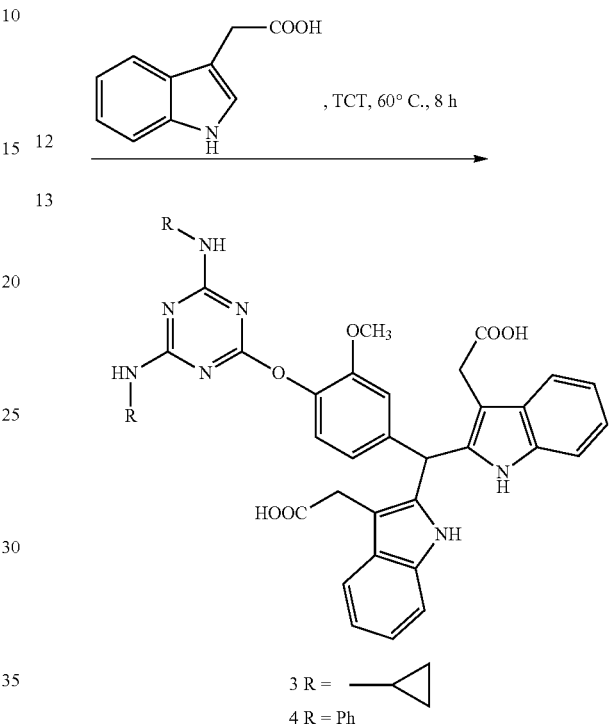

solvent like $CH_2Cl_2$, $CHCl_3$, ethylene dichloride or without a solvent at heating temperature or microwave reaction conditions to provide the compounds with the formulae 3 and 4 respectively (FIG. 1). See example 1, part 4 and example 2, part 4 for the exemplary reaction conditions for the preparative methods of 3 and 4 (Scheme II).

Scheme II further exemplifies the synthetic method for the preparation of compounds of formulae 3 and 4 as shown FIG. 1, with the general structural formula as shown in Formula I, wherein, R=H, Y=$R^1$=methyl, X=a disubstituted triazine with $R^2$=$R^3$=is represented either by a cyclopropyl amine group or aniline group, Z=$CH_2COR^4$ wherein, $R^4$ is represented by OH group, $R^5$=H. In the present invention, compounds with the structural formulae 12 and 13 (see Scheme I, examples 1 and 2, part 2), were independently reacted with indole 3-acetic acid in the presence of acid conc. HCl, aq. HCl solution, HCl gas generated in situ, HCl gas generated in situ from the like of trichlorotriazine (TCT), or Lewis acids like $BF_3OEt_4$, $ZrCl_4$, $BiCl_3$, $AlCl_3$, $InCl_3$ or the like in a suitable Scheme III further exemplifies the synthetic method for the preparation of compounds of formulae 5 and 6 as shown FIG. 1, with the general structural formula as shown in Formula I, wherein, R=H, X=$R^1$=methyl, Y=a disubstituted triazine with $R^2$=$R^3$=is represented either by a cyclopropyl amine group or aniline group, Z=H, $R^5$=H. As exemplified in Scheme III, the triazine derivatives 10 and 11 (See Scheme I, examples 1 and 2, part 1) were independently reacted appropriately with an aldehyde like isovaniline in a suitable solvent such as acetone, methyl ketone and other ketone solvents or Dimethyl formamide, NMP, dimethyl acetamide or the like in the presence of a base for e.g.: potassium carbonate, sodium hydroxide, potassium hydroxide, sodium hydride, potassium hydride, or the like for a suitable time 4-12 h and temperature varying from 50 100° C. to provide the respective compounds 14 and 15. The exemplary reaction conditions for the preparation of 14 are described in example 3, part 1, while, example 4, part 1 describes 15 (Scheme III).

Scheme III

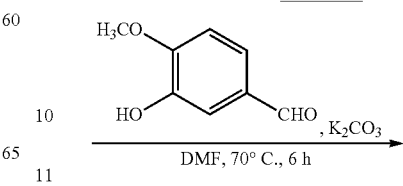

-continued

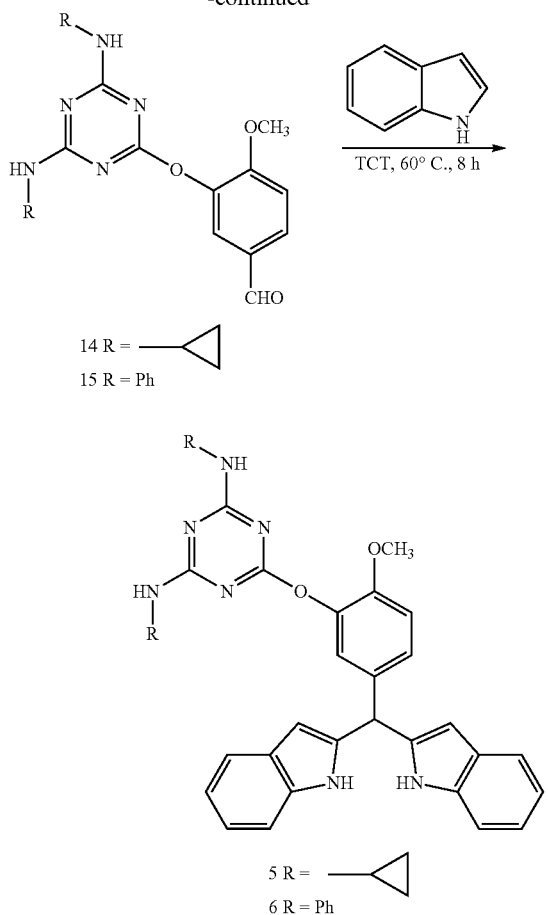

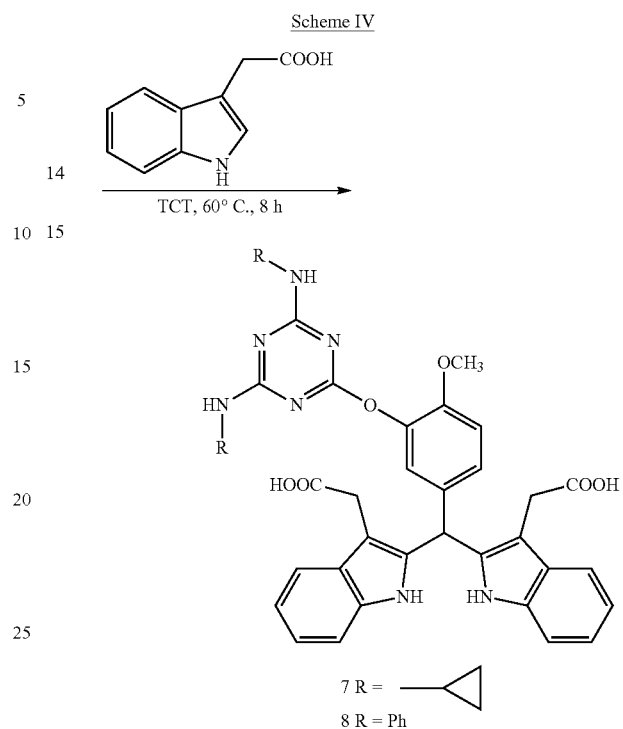

Scheme III further exemplifies the synthetic method for the preparation of compounds of formulae 5 and 6 (FIG. 1), wherein, compounds 14 and 15 (See Scheme III, examples 3 and 4, part 1) were independently reacted in the presence of HCl gas generated in situ from the like of trichlorotriazine (TCT), or an acid conc. HCl, aq. HCl solution, HCl gas generated in situ, or Lewis acids like $BF_3OEt_2$, $ZrCl_4$, $BiCl_3$, $AlCl_3$, $InCl_3$ or the like in a suitable solvent like $CH_2Cl_2$, $CHCl_3$, ethylene dichloride or without a solvent at heating temperature or microwave reaction conditions to obtain the bis-indoles 5 and 6 (FIG. 1) respectively. The exemplary reaction conditions for the preparation of 5 are described in example 3, part 2, while, while for the reaction conditions for 6 see the example 4, part 2 (Scheme III).

Scheme IV exemplifies the synthesis of compounds of formulae 7 and 8 as shown FIG. 1, with the general structural formulae as shown in Formula I, wherein, R=H, X=$R^1$=methyl, Y=a disubstituted triazine with $R^2$=$R^3$=is represented either by a cyclopropyl amine group or aniline group, Z=$CH_2COR^4$ wherein, $R^4$ is represented by OH group, $R^5$=H. As exemplified in the present invention, the aldehydes 14 and 15 (see Scheme III, examples 3 and 4, part 1), independently on reaction with indole 3-acetic acid in the presence of HCl gas generated in situ from the like of trichlorotriazine (TCT), or conc. HCl, aq. HCl solution, HCl gas generated in situ, or Lewis acids like $BF_3OEt_2$, $ZrCl_4$, $BiCl_3$, $AlCl_3$, $InCl_3$ or the like in a suitable solvent like $CH_2Cl_2$, $CHCl_3$, ethylene dichloride or without a solvent at heating temperature or microwave reaction conditions provided access to the 'triazine-aryl-bis-indole' compounds with the structural formulae 7 and 8 (FIG. 1) respectively. For the exemplary reaction conditions for the preparative methods of 7 and 8, see the example 3, part 3 and example 4, part 3 respectively (Scheme IV).

The synthetic protocols developed in the present invention as exemplified in the Schemes I-IV are adoptable for the synthesis of a diversified novel 'triazine-aryl-bis-indole' class of compounds as represented by formula I. These novel compounds belonging to the 'triazine-aryl-bis-indole' class described in the present invention are useful for numerous therapeutic applications. The thus described novel compounds of the present invention, can be administered for the therapeutical applications by different ways such as orally, intravenously and other routes.

The synthetic routes that are presented in the invention as exemplified in Schemes I-IV can be effectively utilized for the synthesis of the novel class of new compounds represented by Formula I, wherein, R=H, Y=$R^1$=methyl, in X, $R^2$=$R^3$=cyclopropyl amine, Z=H, $R^5$=H, represented by structure 1 (FIG. 1) is synthesized.

Similarly, compound with formula R=H, Y=$R^1$=methyl, in X, $R^2$=$R^3$=cyclopropyl amine, Z=$CH_2COR^4$ wherein, $R^4$ is represented by OH group, $R^5$=H, represented by structure 3 (FIG. 1) is synthesized.

Similarly is synthesized the compound with formula wherein, R=H, Y=$R^1$=methyl, in X, $R^2$=$R^3$=NHPh, Z=H, $R^5$=H, represented by structure 2 (FIG. 1) is synthesized.

Similarly, compound with formula R=H, Y=$R^1$=methyl, in X, $R^2$=$R^3$=NHPh, Z=$CH_2COR^4$ wherein, $R^4$ is represented by OH group, $R^5$=H, represented by structure 4 (FIG. 1) is synthesized.

Further, is synthesized a compound with the formula wherein, R=H, X=$R^1$=methyl, in Y, $R^2$=$R^3$=cyclopropyl amine, Z=H, $R^5$=H, represented by structure 5 (FIG. 1) is synthesized.

Similarly, compound with formula R=H, X=R¹=methyl, in Y, R²=R³=cyclopropyl amine, Z=CH₂COR⁴ wherein, R⁴ is represented by OH group, R⁵=H, represented by structure 7 (FIG. 1) is synthesized.

Further, a compound with the formula R=H, X=R¹=methyl, in Y, R²=R³=NHPh, Z=H, R⁵=H, represented by structure 6 (FIG. 1) is synthesized.

Similarly, compound with formula R=H, X=R¹=methyl, in Y, R²=R³=NHPh, Z=CH₂COR⁴ wherein, R⁴ is represented by OH group, R⁵=H, represented by structure 8 (FIG. 1) is synthesized.

The above protocols described in the present invention can be utilized similarly for the synthesis of numerous analogues of 'triazine-aryl-bis-indole' class of novel compounds represented by Formula I.

Figure 9:
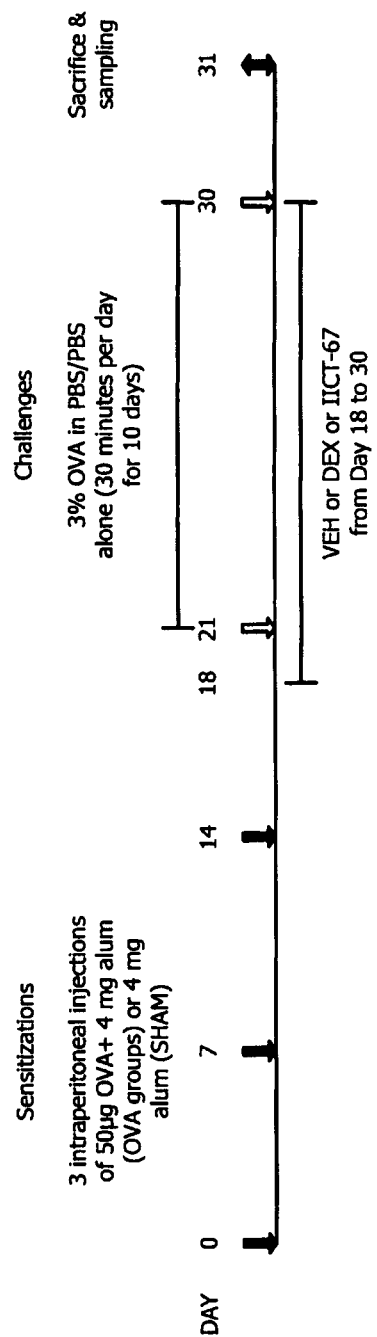
FIG. 9 is a timeline of an evaluation of the antiasthma property of compound 7 (IICT-TA67) on the asthma features in mice.

Scheme V
With reference to FIG. 9, mice were sensitized with ovalbumin (OVA) intraperitoneally (i.p.) on days 0, 7 and 14 as shown in scheme V. Sham group mice were sensitized with only alum dissolved in PBS. From day 21 to 30, mice were exposed to aerosol of OVA (3%) inhalation 25 minutes daily in a Plexiglas chamber (20×20×10 cm³).

For screening experiments, mice divided randomly after acclimatization into 6 groups, each group (n=4-5) was named according to sensitization/challenge/treatment: Group I was alum sensitized, saline challenged and treated with vehicle (SHAM/SAL/VEH), group II was OVA sensitized, OVA challenged and treated with DMSO as vehicle (OVA/OVA/VEH), group III, IV, V were OVA sensitized, OVA challenged and treated with 0.1, 1and 10 mg/kg IICT-67 and group VI was OVA sensitized, OVA challenged and treated with 0.75 mg dexamethasone (OVA/OVA/DEX). Compound 7 (IICT-TA67) was dissolved in DMSO. So DMSO was used as a vehicle. IICT-TA67 or DEX was given orally twice per day in the volume of 10 μl.

Airway responsiveness was measured by barometric plethysmography using whole-body plethysmography (WBP; Buxco, Troy, N.Y.) 12 hours after last saline or ovalbumin challenge. At the time of measurement the animals were awake and breathing spontaneously. Enhanced pause (Penh) to methacholine as measured using barometric plethysmography is a valid indicator of bronchoconstriction in mice and can be used to measure AHR.

Figure 2:
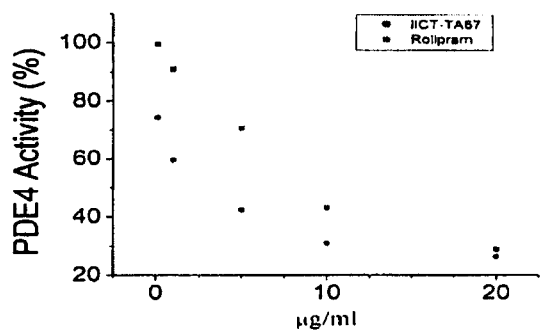
FIG. 2 is related to the screening of the above novel class of compounds (1-8) as PDE-4 inhibitors.

FIG. 2. Inhibition of phosphodiesterase 4 activity by IICT-TA67 in vitro. To examine whether IICT-TA67 inhibits PDE-4 activity in vitro, enzyme preparations were incubated in the absence or presence of different concentrations (1-20 μg/ml) of IICT-TA67 and breakdown of cAMP was monitored by β counter. IICT-TA67 inhibited PDE4 activity in a dose dependent manner (0.1-20 μg/ml) which was compared with known PDE4 inhibitor, rolipram.

Table 1. Measurement of phosphodiesterase (PDE)-4 activity by compounds. The enzyme preparations were incubated in the absence or presence of a 10 μg/ml) of compounds 1-8 and 10-13 and breakdown of cAMP was monitored by β counter. PDE 4 activity was compared with known PDE4 inhibitor, rolipram.

Figure 3:
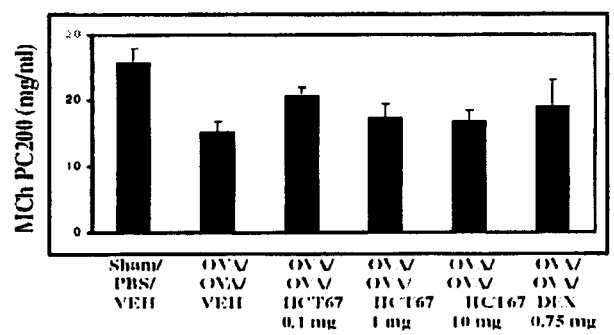
FIG. 3 illustrates inhibition of Airway hyper-responsiveness to evaluate anti-asthmatic effect in vivo by compound 7 (IICT-TA67).

FIG. 3. Inhibition of airway hyperresponsiveness (AHR) in mouse model of asthma by IICT-TA67. To evaluate the antiasthma property of IICT-TA67 on the asthma features, BALB/c mice were sensitized and challenged with ovalbumin (OVA) as shown in Scheme V to develop asthmatic features such as airway hyperreactivity (AHR) to methacholine (MCh). The sensitized and challenged mice were treated with different concentrations of IICT-67. AHR was measured after allergen challenge with increasing concentrations of methacholine and MChPC200 was calculated. As shown in FIG. 2, MChPC200 was decreased significantly in asthmatic controls (OVA/OVA/VEH) compared to normal control mice (SHAM/PBS/VEH). This indicates that OVA/OVA/VEH mice have developed marked bronchoconstriction. However, treatment with IICT-TA67 significantly attenuated the decrease in MChPC200 and maximum effect was found with 0.1 mg/kg dose. This reduction was comparable with dexamethasone treatment (OVA/OVA/DEX).

Figure 4:
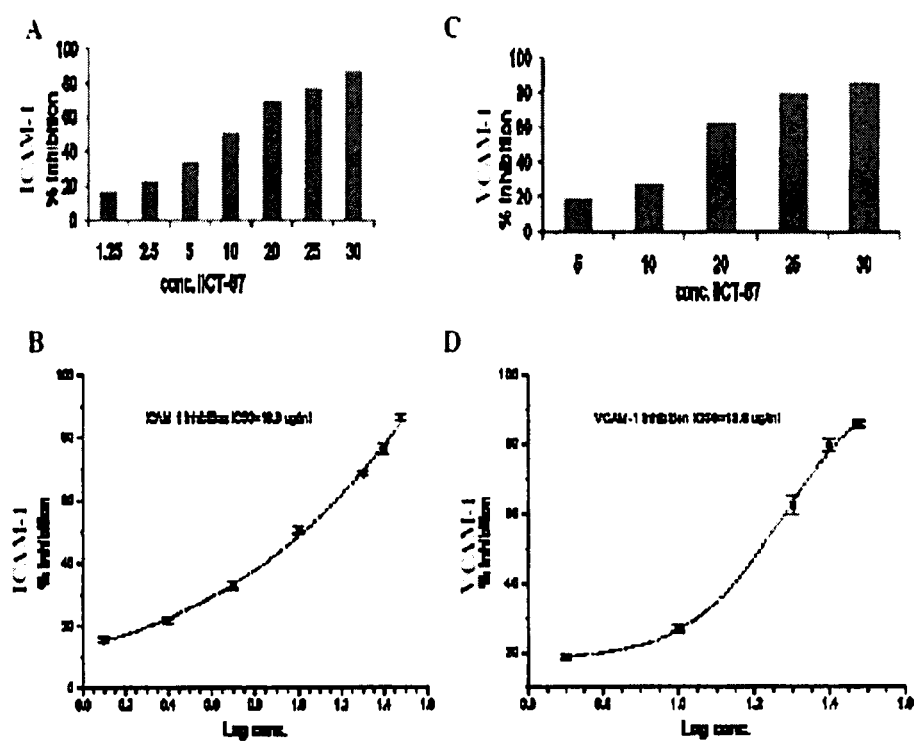
FIG. 4 deals with inhibition of TNF alpha induced expression of intracellular cell adhesion molecule Intercellular Adhesion Molecule type 1 (ICAM-1) and Vascular Cell Adhesion Molecule type 1(VCAM-1) in vitro by IICT-TA67.

FIG. 4. Inhibition of TNF-α induced expression Intercellular Adhesion Molecule type 1 (ICAM-1) and Vascular Cell Adhesion Molecule type 1 (VCAM-1) on HUVECs by IICT-TA67. To determine the effect of IICT-TA67 on TNF-α induced cell adhesion molecules such as ICAM-1 and VCAM-1, HUVECs were pretreated with various concentrations of IICT-TA67 for 2 hours followed by induction with TNF-α for 16 hours. The cell surface expression of cell adhesion molecules was measured by ELISA. As shown in FIG. 2, IICT-TA67 inhibits the expression of intracellular cell adhesion molecule type 1 ($IC_{50}$=10.6 μg/ml) and vascular cell adhesion molecule type 1 ($IC_{50}$=16.6 μg/ml) in a dose dependent manner on the surface of TNF-alpha stimulated human endothelial cells.

Figure 5:
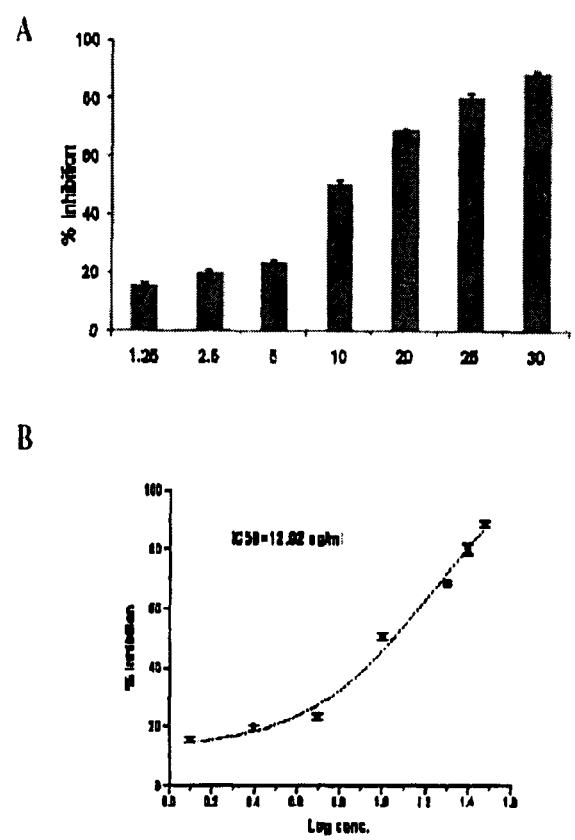
FIG. 5 is related to the inhibition of adhesion of Neutrophils by IICT-TA67.

FIG. 5. IICT-TA67 inhibits the adhesion of Neutrophils on TNF-alpha induced HUVECs. To study whether the inhibition of Intercellular Adhesion Molecule type 1 (ICAM-1) and Vascular Cell Adhesion Molecule type 1(VCAM-1) functionally correlates with the inhibition of adhesion of neutrophils to the endothelial monolayer, neutrophil adhesion assay was performed. For this, HUVECs were pretreated with various concentrations of IICT-TA67 for 2 hours followed by induction with TNF-α for 6 hours. Human blood neutrophils were added onto the endothelial cells monolayer and allowed to adhere for one hour at 37° C. The number of cells that remained adhered to the monolayer was estimated by measuring the peroxidase activity. As shown in FIG. 3, IICT-TA67 dose dependently inhibits the adhesion of human neutrophils to the endothelial monolayer ($IC_{50}$=12.02 μg/ml).

Figure 6:
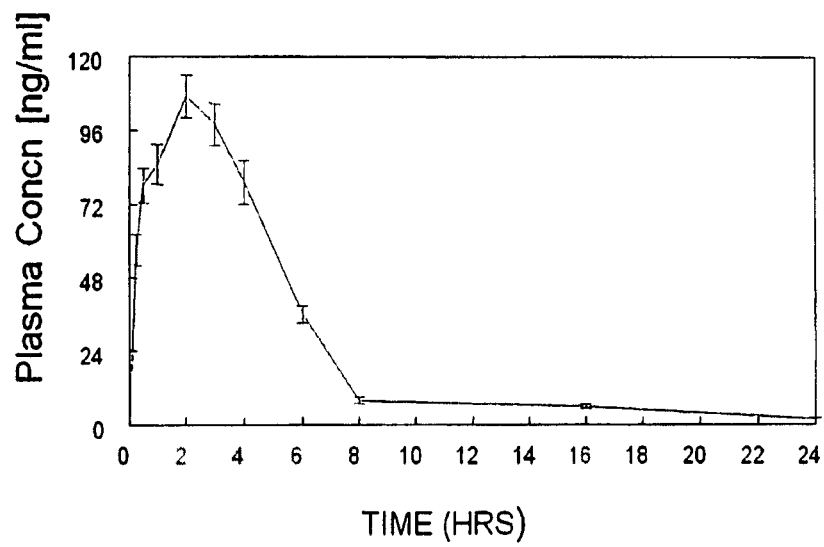
FIG. 6. Pharmacokinetics of the compound 7 (IICT-TA67) administered through oral route.
Figure 7:
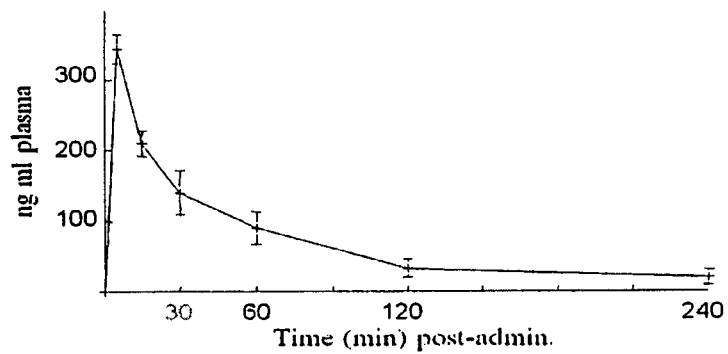
FIG. 7. Pharmacokinetics of the compound 7 (IICT-TA67) administered intravenous route.

FIG. 6. Pharmacokinetics of IICT-TA67 through oral route.
FIG. 7. Pharmacokinetics of IICT-TA67 through intravenous (i.v) route in mice. IICT-TA67 (20 mg/kg) was administered orally (or 10 mg/kg by i.v. route) as a fine suspension in 1% Gum acacia. Blood samples were drawn from retro-orbital plexus at designated times in pre-labeled heparinised tubes and centrifuged (3500 rpm×10 minutes) to obtain the plasma. Blood samples were collected at 0, 5, 15 and 30 min, and 1, 2, 4, 6, 8, 16 and 24 hrs post-administration after oral/iv route. HPLC determinations were done on Shimadzu chromatograph (Model: LC-10 Atvp equipped with a diode array detector). The Molecule ICT-TA67 was determined at 276 nm using RP-18 column (5 μm×25 cm). Mobile phase consisted of acetonitrile: water (55:45) with a flow rate of 1.0 ml/min.

Table 2. PK Constants for Molecule IICT-TA67
Values are derived from plasma drug concentration-time profile curves of TA-67 as depicted in FIGS. 6 and 7.

Figure 8:
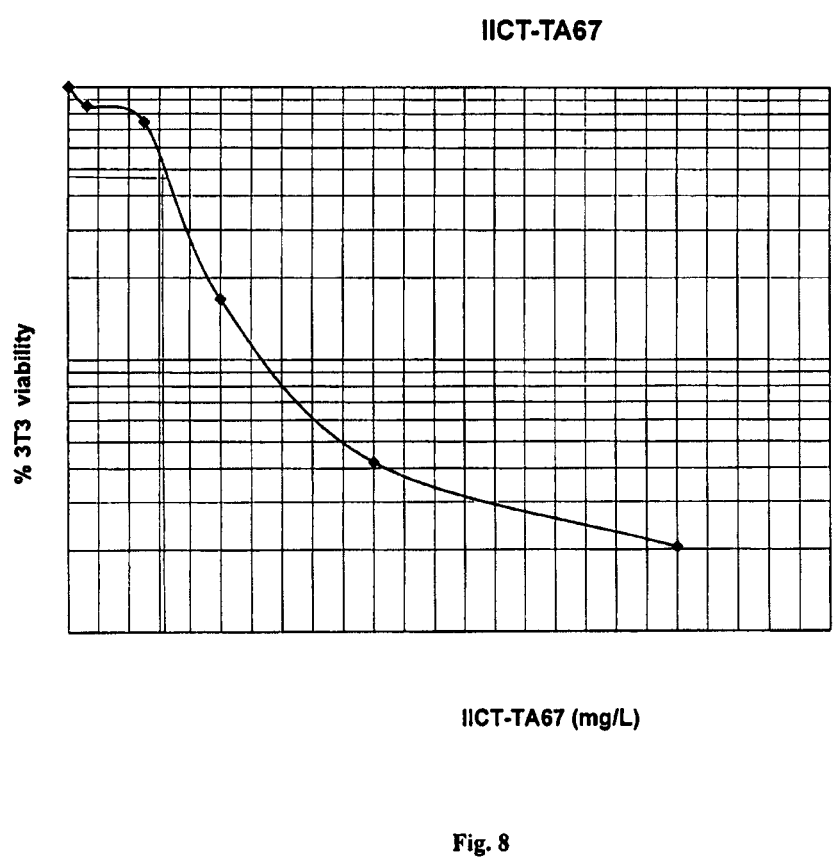
FIG. 8. Toxicity data of compound 7 (IICT-TA67).

FIG. 8. IICT-TA67 is not toxic. To evaluate the cytotoxicity of test chemical (IICT-TA67) BALB/c 3T3 cell line was used for Neutral Red Uptake (NRU) cytotoxicity test. The test result has been used to determine $IC_{50}$ for IICT-TA67 and acute oral toxicity ($LD_{50}$) in rodent was predicted. The predicted $LD_{50}$ for acute oral toxicity of IICT-TA67 in rodent is found to 430 mg/kg body weight.

The following non-limiting examples are illustrative of the present invention.

EXAMPLE 1

General procedure for the preparation of 2,2'-[2,2'-4-(4,6-bis-cyclopropylamino)-1,3,5-triazin-2-yl-oxy-3-methoxyphenyl]-methylene-bis-1H-indole 1 and 2,2'-[2,2'-4-(4,6-bis-cyclopropylamino)-1,3,5-triazin-2-yl-oxy-3-methoxyphenyl]-methylene-bis-(1H-indole-3,3-diyl)-diacetic acid 3 (Scheme I-Compound 1; Scheme II-Compound 3).

Part 1: 6-Chloro-$N^2,N^4$-dicyclopropyl-1,3,5-triazine-2,4-diamine (Scheme I-Compound 10).

A fine slurry prepared from cyanuric chloride 9 (5.0 g, 27.17 mmol) by the addition of acetone (25 mL) was stirred at 40° C. for 30 min. The reaction mixture was cooled to 0° C. and treated with cyclopropyl amine (3.09 g, 54.34 mmol). It was stirred at the same temperature for 1 h and neutralized with aq. 1N NaOH till the reaction mixture becomes basic. It was then heated to 40° C. and stirred at this temperature for 2 h. The reaction mixture was filtered, washed with acetone (3×25 mL), evaporated solvent and dried under vacuum to furnish 10 (5.6 g, 91.6%).

Part 2: 4-[4,6-Bis-cyclopropylamino-1,3,5-triazin-2-yl-oxy]-3-methoxy benzaldehyde (Scheme I-Compound 12)

A mixture of 10 (5.0 g, 22.1 mmol), vaniline (4.04 g, 26.6 mmol) and $K_2CO_3$ (9.17 g, 66.48 mmol) in DMF (30 mL) was heated at 70° C. for 6 h. The reaction mixture was cooled to room temperature, diluted with water (75 mL) and extracted with EtOAc (4×50 mL). The combined organic layers were washed with water (50 mL), brine (50 mL) and dried ($Na_2SO_4$). Evaporation of the solvent under reduced pressure and purification of the residue by column chromatography (Silica gel, EtOAc in hexane 3:7) furnished 12 (5.58 g, 73.7%) as a white solid.

Part 3: 2,2'-[2,2'-4-(4,6-Bis-cyclopropylamino)-1,3,5-triazin-2-yl-oxy-3-methoxyphe-nyl]-methylene-bis-1H-indole (Scheme I-Compound 1)

To a stirred solution of 12 (1.0 g, 2.9 mmol) and indole (0.69 g, 5.8 mmol) in $CH_3CN$ (5 mL), 10 mol % cyanuric chloride (18 mg) was added and heated at 60° C. for 8 h. The reaction mixture was cooled to room temperature, diluted with water (25 mL) and extracted with EtOAc (4×50 mL). The combined organic layers were washed with water (50 mL), brine (50 mL) and dried ($Na_2SO_4$). Evaporation of the solvent under reduced pressure and purification of the residue by column chromatography (Silica gel, EtOAc in hexane 1:4) afforded 1 (1.25 g, 76.2%) as a pale brown solid.

Part 4: 2,2'-[2,2'-4-(4,6-Bis-cyclopropylamino)-1,3,5-triazin-2-yl-oxy-3-methoxyphe-nyl]-methylene-bis-(1H-indole-3,3-diyl)-diacetic acid (Scheme II-Compound 3)

A mixture of 12 (1.0 g, 2.9 mmol) and indole 3-acetic acid (1.02 g, 5.86 mmol) in $CH_3CN$ (5 mL) was treated with 10 mol % cyanuric chloride (18 mg) and heated at 60° C. for 8 h. The reaction mixture was cooled to room temperature, diluted with water (25 mL) and extracted with EtOAc (4×50 mL). The combined organic layers were washed with water (50 mL), brine (50 mL) and dried ($Na_2SO_4$). Evaporation of the solvent under reduced pressure and purification of the residue by column chromatography (Silica gel, EtOAc in hexane 1:4) afforded 3 (1.02 g, 51.7%) as a pale brown solid.

EXAMPLE 2

Preparation of 2,2'-[2,2'-4-(4,6-bis-anilino)-1,3,5-triazin-2-yl-oxy-3-methoxyphenyl]-methylene-bis-1H-indole 2 and 2,2'-[2,2'-4-(4,6-bis-anilino)-1,3,5-triazin-2-yl-oxy-3-methoxyphenyl]-methylene-bis-(1H-indole-3,3-diyl)-diacetic acid 4 (Scheme I-Compound 2; Scheme II-Compound 4).

Part 1: 6-Chloro-$N^2,N^4$-diphenyl-1,3,5-triazine-2,4-diamine (Scheme I-Compound 11)

A fine slurry prepared from cyanuric chloride 9 (5.0 g, 27.17 mmol) by the addition of acetone (25 mL) was stirred at 40° C. for 30 min. The reaction mixture was cooled to 0° C. and treated with aniline (5.05 g, 54.34 mmol) and worked up as described for 10 to furnish 11 (7.45 g, 98.0%).

Part 2: 4-[4,6-Bis-anilino-1,3,5-triazin-2-yl-oxy]-3-methoxy benzaldehyde (Scheme I-Compound 13)

A mixture of 11 (5 g, 16.79 mmol), vaniline (3.06 g, 20.15 mmol) and $K_2CO_3$ (9.17 g, 66.51 mmol) in DMF (30 mL) was heated at 70° C. for 6 h. Work up and purification as described for 12 gave 13 (6.05 g, 87.1%) as a white solid.

Part 3: 2,2'-[2,2'-4-(4,6-Bis-anilino)-1,3,5-triazin-2-yl-oxy-3-methoxyphenyl]-methylene-bis-1H-indole (Scheme I-Compound 2)

To a stirred solution of 13 (1.0 g, 2.42 mmol) and indole (0.56 g, 4.84 mmol) in $CH_3CN$ (5 mL), 10 mol % cyanuric chloride (18 mg) was added and heated at 60° C. for 8 h. Work up and purification as described for 1 furnished 2 (1.0 g, 60.9%) as a pale brown solid.

Part 4: 2,2'-[2,2'-4-(4,6-Bis-anilino)-1,3,5-triazin-2-yl-oxy-3-methoxyphenyl]-methylene-bis-(1H-indole-3,3-diyl)-diacetic acid (Scheme II-Compound 4)

A mixture of 13 (1.0 g, 2.41 mmol) and indole 3-acetic acid (0.84 g, 4.83 mmol) in $CH_3CN$ (5 mL) was treated with 10 mol % cyanuric chloride (18 mg) and heated at 60° C. for 8 h. The reaction mixture was worked up and purified as described for 3 to give 4 (1.02 g, 56.6%) as a pale brown solid.

EXAMPLE 3

Preparation of 2,2'-[2,2'-3-(4,6-bis-cyclopropylamino)-1,3,5-triazin-2-yl-oxy-4-methoxyphenyl]-methylene-bis-1H-indole 5 and 2,2'-[2,2'-3-(4,6-bis-cyclopropyl-amino)-1,3,5-triazin-2-yl-oxy-4-methoxyphenyl]-methylene-bis-(1H-indole-3,3-diyl)-diacetic acid 7 (Scheme III-Compound 5; Scheme IV-Compound 7).

Part 1: 4-[4,6-Bis-cyclopropylamino-1,3,5-triazin-2-yl-oxy]-4-methoxy benzaldehyde (Scheme III-Compound 14)

A mixture of 10 (5.0 g, 22.1 mmol), isovaniline (4.04 g, 26.6 mmol) and $K_2CO_3$ (9.17 g, 66.51 mmol) in DMF (30 mL) was heated at 70° C. for 6 h. Work up and purification as described for 12 furnished 14 (6.2 g, 82.1%) as a white solid.

Part 2: 2,2'-[2,2'-3-(4,6-Bis-cyclopropylamino)-1,3,5-triazin-2-yl-oxy-4-methoxyphe-nyl]-methylene-bis-1H-indole (Scheme III-Compound 5)

To a stirred solution of 14 (1.0 g, 2.9 mmol) and indole (0.68 g, 5.85 mmol) in $CH_3CN$ (5 mL), 10 mol % cyanuric chloride (18 mg) was added and heated at 60° C. for 8 h. Workup and purification as described for 1 gave 5 (1.1 g, 67.1%) as a pale brown solid.

Part 3: 2,2'-[2,2'-3-(4,6-Bis-cyclopropylamino)-1,3,5-triazin-2-yl-oxy-4-methoxyphe-nyl]-methylene-bis-(1H-indole-3,3-diyl)-diacetic acid (Scheme IV-Compound 7)

A mixture of 14 (1.0 g, 2.9 mmol) and indole 3-acetic acid (1.02 g, 5.85 mmol) in $CH_3CN$ (5 mL) was treated with 10 mol % cyanuric chloride (18 mg) and heated at 60° C. for 8 h. Work up and purification as described for 3 furnished 7 (1.2 g, 60.9%) as a pale brown solid.

EXAMPLE 4

Preparation of 2,2'-[2,2'-3-(4,6-bis-anilino)-1,3,5-triazin-2-yl-oxy-4-methoxyphenyl]-methylene-bis-1H-indole 6 and 2,2'-[2,2'-3-(4,6-bis-anilino)-1,3,5-triazin-2-yl-oxy-4-methoxyphenyl]-methylene-bis-(1H-indole-3,3-diyl)-diacetic acid 8 (Scheme I-Compound 6; Scheme II-Compound 8)

Part 1: 4-[4,6-Bis-anilino-1,3,5-triazin-2-yl-oxy]-4-methoxy benzaldehyde (Scheme III-Compound 15)

A mixture of 11 (5 g, 16.79 mmol), isovaniline (3.06 g, 20.15 mmol) and $K_2CO_3$ (6.95 g, 50.38 mmol) in DMF (30 mL) was heated at 70° C. for 6 h. Work up and purification as described for 12 gave 15 (6.01 g, 86.7%) as a white solid.

Part 2: 2,2'-[2,2'-3-(4,6-Bis-anilino)-1,3,5-triazin-2-yl-oxy-4-methoxyphenyl]-methylene-bis-1H-indole (Scheme III-Compound 6)

To a stirred solution of 15 (1.0 g, 2.4 mmol) and indole (0.56 g, 4 8 mmol) in $CH_3CN$ (5 mL), 10 mol % cyanuric chloride (18 mg) was added and heated at 60° C. for 8 h. Work up and purification as described for 1 furnished 6 (1.0 g, 65.7%) as a pale brown solid.

Part 3: 2,2'-[2,2'-3-(4,6-Bis-anilino)-1,3,5-triazin-2-yl-oxy-4-methoxyphenyl]-methylene-bis-(1H-indole-3,3-diyl)-di-acetic acid (Scheme IV-Compound 8)

A mixture of 13 (1.0 g, 2.4 mmol) and indole 3-acetic acid (0.85 g, 4.8 mmol) in $CH_3CN$ (5 mL) was treated with 10 mol % cyanuric chloride (18 mg) and heated at 60° C. for 8 h. The reaction mixture worked up and purified as described for 3 to give 8 (1.15 g, 63.8%) as a pale brown solid.

EXAMPLE 5

Determination of PDE-4 Activity In Vitro

For phosphodiesterase (PDE-4) assay, enzyme preparations were performed from rat heart (Ko et al 2004, Biochemical Pharmacology 68:2087-2094). Heart was excised from anesthetized rat and transfer into normal saline solution. Heart weighing 687 mg was taken and homogenized in 2.5 volumes of homogenization buffer containing 20 mM Tris-Cl, 50 mM NaCl, 2 mM EDTA, 0.1 mM PMSF, 1 mH DTT, protease inhibitors 1 µg/µl. The homogenate was centrifuged at 500×g for 5 minute at 4° C. Then sup was taken for further centrifuged at 40,000×g for 30 minute (ultra centrifugation). After centrifugation supernatant was collected for phosphodiesterase assay. Protein concentration was estimated and for each assay, 2.5 µg protein (PDE enzyme preparation) was used. All compounds tested for PDE 4 activity were dissolved in DMSO.

Phosphodiesterase 4 assay: Phosphodiesterase 4 assay was conducted with [$^3$H] cAMP SPA enzyme assay (GE Amersham, UK) using 2.5 µg enzyme preparation for each well. Into each well 60 µl water, 10 µl assay buffer supplied with the kit, 10 µl compound (inhibitor), 10 µl PDE enzyme or homogenizing buffer (blank) and 10 µl radiolabel led cAMP ([$^3$H] cAMP, GE Amersham, UK) were added. To check activity of the enzyme without inhibitor 10 µl DMSO was added in place of inhibitor to a separate well. The reaction mixtures were incubated for 30 mi at 30° C. The reaction was stopped by adding 50 µl SPA bead supplied with the kit. It was then mixed well and allowed to stand at room temperature for 20 min. Breakdown of cAMP in each tube was monitored by β counter. The reading in each tube was obtained in counts per minute (CPM). The reading of the blank tube (without enzyme) was subtracted from each tube to normalize the counts. The enzyme activity was calculated by considering the CPM reading without any inhibitor (compound) as 100. The results are summarized in Table 1.

As shown in Table 1 all the compounds inhibited PDE 4 activity which is comparable to known PDE4 inhibitor, rollipram. There was a 60% inhibition of PDE 4 activity by IICT-TA67 at 10 µg/ml concentration.

TABLE 1

| Compound no. | Name | Dose | Inhibition % |
|---|---|---|---|
| 1: | IICT-TA44 | 10 µg/ml | 16 |
| 2 | IICT-TA59 | 10 µg/ml | 34 |
| 3 | IICT-TA45 | 10 µg/ml | 42 |
| 4 | IICT-TA60 | 10 µg/ml | 31 |
| 5 | IICT-TA66 | 10 µg/ml | 34 |
| 6 | IICT-TA77 | 10 µg/ml | 45 |
| 7 | IICT-TA67 | 10 µg/ml | 60 |
| 8 | IICT-TA78 | 10 µg/m1 | 73 |
| 10 | IICT-TA42 | 10 µg/m1 | 44 |
| 11 | IICT-TA57 | 10 µg/m1 | 53 |
| 12 | IICT-TA43 | 10 µg/m1 | 29 |
| 13 | IICT-TA58 | 10 µg/m1 | 30 |
| Rolipram | | 10 µg/ml | 69 |

EXAMPLE 6

Protocol for In Vivo Test in Asthma Model in Mice (Scheme V)

Step 1: Sensitization and Challenge

Mice were sensitized with 0.2 ml PBS containing 50 µg ovalbumin (OVA) (Sigma, USA) and 4 mg aluminum hydroxide in saline intraperitonially (i.p.) on days 0, 7 and 14 as shown in scheme V. Sham group mice were sensitized with only alum dissolved in PBS. From day 21 to 30, mice were exposed to aerosol of OVA (3%) inhalation 25 minutes daily in a Plexiglas chamber (20×20'10 $cm^3$). The aerosol was generated by a nebulizer (OMRON CX, model) with an airflow rate of 9 L/minute. Sham group mice were challenged with PBS alone.

Step 2: Mice grouping and treatment with IICT-TA67

There were two set of experiments: i) screening experiments with different concentrations of IICT-67 and ii) confirmatory experiments. For screening experiments, mice were divided randomly after acclimatization into 6 groups, each group (n=4-5) was named according to sensitization/challenge/treatment: Group I was alum sensitized, saline challenged and treated with vehicle (SHAM/SAL/VEH), group II was OVA sensitized, OVA challenged and treated with DMSO as vehicle (OVA/OVA/VEH), group III, IV, V were OVA sensitized, OVA challenged and treated with 0.1, 1 and 10 mg/kg IICT-67 and group VI was OVA sensitized, OVA challenged and treated with 0.75 mg dexamethasone (OVA/OVA/DEX). Compound 7 (IICT-TA67) was dissolved in DMSO. So DMSO was used as a vehicle. IICT-TA67 or DEX was given orally twice per day in the volume of 10 µl. Confirmatory experiments were done once with 0.1 mg/kg IICT-TA67 with 6 mice in each group.

Step 3: Determination of Airway Responsiveness

Airway responsiveness was measured by barometric plethysmography using whole-body plethysmography (WBP; Buxco, Troy, N.Y.) 12 hours after last saline or ovalbumin challenge. At the time of measurement the animals were awake and breathing spontaneously. Enhanced pause (Penh) to methacholine as measured using barometric plethysmography is a valid indicator of bronchoconstriction in mice and can be used to measure AHR. Baseline pen H was taken initially, and then PBS followed by increasing concentrations (0-16 mg/ml) of methacholine was nebulized through an inlet of the main chamber for 3 min. Readings were taken and averaged for 5 minutes from the starting time of nebulisation. Airway responsiveness to MCh was evaluated by the concentration of MCh required to increase the Pen H to twice the baseline value (MCh $PC_{200}$). The results are presented in FIG. 3.

As shown in FIG. 3, MChPC200 was decreased significantly in asthmatic controls (OVA/OVA/VEH) compared to normal control mice (SHAM/PBS/VEH). This indicates that OVA/OVA/VEH mice have developed marked bronchoconstriction. However, treatment with IICT-TA67 significantly attenuated the decrease in MChPC200 and maximum effect was found with 0.1 mg/kg dose (FIG. 3). This reduction was comparable with dexamethasone treatment (OVA/OVA/DEX).

EXAMPLE 7

Cell-Elisa for Measurement of Intercellular Adhesion Molecule type 1 (ICAM-1) and Vascular Cell Adhesion Molecule Type 1(VCAM-1)

Cell-ELISA was used for measuring the expression of ICAM-1 on surface of endothelial cells. Endothelial cells were incubated with or without IICT-TA67 at desired concentrations for the required period, followed by treatment with TNF-α (10 ng/ml) for 16 h for ICAM-1 and VCAM-1 expression. The cells were fixed with 1.0% glutaraldehyde. Non-specific binding of antibody was blocked by using skimmed milk (3.0% in PBS). Cells were incubated overnight at 4° C. with anti-ICAM-1 mAb anti-VCAM-1 antibody, diluted in blocking buffer, the cells were further washed with PBS and incubated with peroxidase-conjugated goat anti-mouse secondary Abs. After washings, cells were exposed to the peroxidase substrate (o-phenylenediamine dihydrochloride 40 mg/100 ml in citrate phosphate buffer, pH 4.5). Reaction was stopped by the addition of 2 N sulfuric acid and absorbance at 490 nm was measured using microplate reader (Spectramax 190, Molecular Devices, USA).

As shown in FIG. 4, IICT-TA67 inhibits the expression of ICAM-1 ($IC_{50}$=10.6 μg/ml) and VCAM-1($IC_{50}$=16.6 μg/ml) in a dose dependent manner on the surface of TNF-alpha stimulated human endothelial cells.

EXAMPLE 8

Protocol for Neutrophil Isolation

Neutrophils were isolated from peripheral blood of healthy individuals. Blood was collected in heparin solution (20 U/ml) and erythrocytes were removed by sedimentation against 6% dextran solution. Plasma, rich in white blood cells, was layered over Ficoll-Hypaque solution, followed by centrifugation (300 g for 20 min, 20° C.). The top saline layer and the Ficoll-Hypaque layer were aspirated leaving neutrophils/RBC pellet. The residual red blood cells were removed by hypotonic lysis. Isolated cells were washed with PBS and resuspended in PBS containing 5 mM glucose, 1 mM $CaCl_2$, and 1 mM $MgCl_2$. The number of cells were recorded to make a final concentration of $6\times10^5$ cells/ml.

EXAMPLE 9

Protocol for Cell Adhesion Assay

The endothelial cells plated in 96-well culture plates were incubated with or without compound IICT-TA67 at desired concentrations for 2 h, followed by induction with TNF-α (10 ng/ml) for 6 h. Endothelial monolayers were washed with PBS and neutrophils ($6\times10^4$/well) were added over it and were allowed to adhere for 1 h at 37° C. The non-adherent neutrophils were washed with PBS and neutrophils bound to endothelial cells were assayed by adding a substrate solution consisting of o-phenylenediamine dihydrochloride (40 mg/100 ml in citrate phosphate buffer, pH 4.5), 0.1% cetrimethyl ammonium bromide, and 3-amino-1,2,4 triazole (1 mM). The absorbance was read at 490 nm using an automated microplate reader (Model 680, Bio-Rad, USA). The results are presented in FIG. 5. As shown in FIG. 5 IICT-67 dose dependently inhibits the adhesion of human neutrophils to the endothelial monolayer (IC50=12.02 μg/ml).

EXAMPLE 10

Protocol for Pharmacokinetic Study

Animals. Healthy swiss mice of both the sexes (25-30) were used. The animals were kept (3/cage) under controlled conditions (temp 26±2° C.; relative humidity 50±5%; 12 h light/dark cycle) and maintained on pelleted rodent diet (Ashirwad Industries Ltd. Chandigarh, India). Water was provided ad libitum. Institutional Animal Ethics committee approved the animal experiments. Animals were fasted for 16 hours before use.

Step 1: Dosing: IICT-TA67 (20 mg/kg) was administered orally (or 10 mg/kg by i.v.route) as a fine suspension in 1% Gum acacia. Blood samples were drawn from retro-orbital plexus at designated times in pre-labeled heparinised tubes and centrifuged (3500 rpm×10 minutes) to obtain the plasma. Blood samples were collected at 0, 5, 15 and 30 min, and 1, 2, 4, 6, 8, 16 and 24 hrs post-administration after oral/iv route.

Step 2: HPLC determinations: Aliquots of plasma were mixed with acetonitrile (1:2), vortexed for two minutes (2500 rpm) and centrifuge at 5000 rpm for 10 min. The organic layer was collected and evaporated to dryness using solvent evaporator (Model: SPD 111V, Thermo Electron Corporation, MA). The dried samples were reconstituted in mobile phase for HPLC analysis. In a similar manner samples were also prepared from aliquots of plasma collected from untreated animals which were spiked with molecule 67 (0.25 μg-10 μg/ml). These were used to draw calibration curves which were found to be linear ($r^2$=0.9998). Reproducibility of the method was defined by both intra-, and inter-day variance. The retention time of Mol. 67 was 10.688 min, at which no other interfering peak was observed. The lower limit of detection (LOD) was 11 ng/ml; limit of quantitation (LOQ) was 32 ng/ml; recovery was 90±2%.

HPLC determinations were done on Shimadzu chromatograph (Model: LC-10 Atvp equipped with a diode array detector). Molecule 67 was determined at 276 nm using RP-18 column (5 μm×25 cm). Mobile phase consisted of acetonitrile: water (55:45) with a flow rate of 1.0 ml/min.

Step 3: Calculating Bioavailability indices: A concentration-time curve for Molecule 67 was established and pharmacokinetic parameters AUC, $C_{max}$, and $t_{max}$ were determined by a non-compartmental analysis using TOPFIT software package. Absolute bioavailability was determined using the following formula: $AUC_{oral} \times dose_{iv}/AUC_{iv} \times Dose_{oral}$. The results are presented in Table 2.

Non-compartmental analysis of the data showed a Cmax of 107 ng/ml and Tmax of 3 hrs. Other pharmacokinetic constants were as follows: The half-life ($T_{1/2}$ of 4.26 hrs; AUC, 502.75 ng/hr.ml; clearance (CL), 66.1 ml.min, and volume of distribution (Vd) 474 L. After i.v. dosing of 10 mg/kg of TA-67 in mice showed AUC 357.71 ng/hr.ml; $T_{1/2,0.93}$ hrs; CL, 466 ml/min and Vd 37.5 L.

Absolute bioavailability (F) was found to be 0.703.

TABLE 2

| Parameter | Oral | i.v |
|---|---|---|
| Cmax (ng/ml) | 107 | 332 |
| Tmax | 2.0 | 10 min |
| AUC (0-t) ng · hr/ml | 502.75 | 357.71 |
| CL ml/min | 663 | 466 |
| T ½ hr | 4.26 | 1.5 |
| Vd (L) | 474 | 37.5 |

EXAMPLE 11

Protocol for Cytotoxicity Assay

Basal cytotoxicity of IICT-TA67 has been performed to measure $IC_{50}$ and thereafter predict in vivo acute oral $LD_{50}$ values in rodent by using Halle's Registry of cytotoxicity (RC) prediction model: log (LD50)=0.435×log (IC50)+0.625 (Halle, 1998; Spielmann et al., 1999). Balb/c 3T3 Neutral Red Dye Uptake (NRU) cytotoxicity assay procedure was adopted (Liebsch & Spielmann 1995). In brief 3T3 cell were grown in 96 well microtitre plates and exposed to IICT-TA-67. After 48-hour incubation, the test material was removed and Neutral red (NR) solution was applied to the cells. The cells were incubated again, the excess NR solution was removed and finally NR was eluted from the cells. The NRU was determined by using a microtitre plate reader to measure the optical density at 540 nm of the eluted dye in 96 well plate. A calculation of cell viability expressed as NRU was made for each concentration of the test chemical by using the mean NRU of 6 replicate values per test concentration. The cell viability value was compared with the mean NRU of all vehicle control values and relative cell viability was then expressed as percent of untreated vehicle control. The results are presented in FIG. 8. As shown in FIG. 8 IICT-67 does not seem to be toxic to endothelial cells. Although the percentage of viability is slightly more than 95% at 50 µg/ml of IICT-67, 30 µg/ml (% viability of cells is 98%)

We claim:

1. A triazine-aryl-bis-indole compound selected from one of:

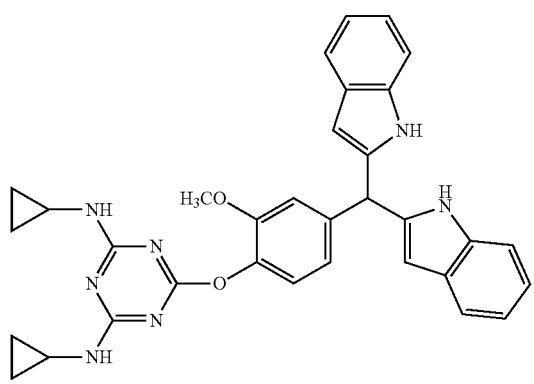

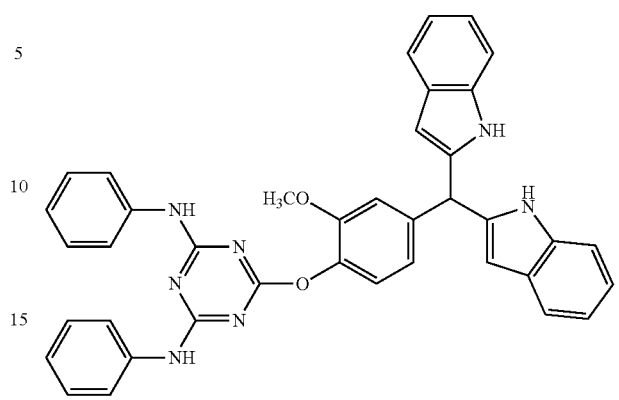

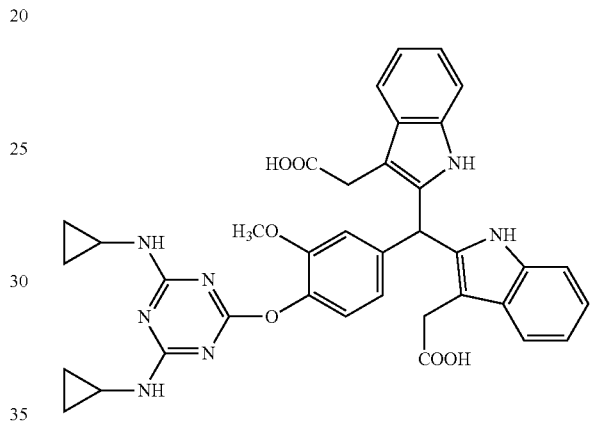

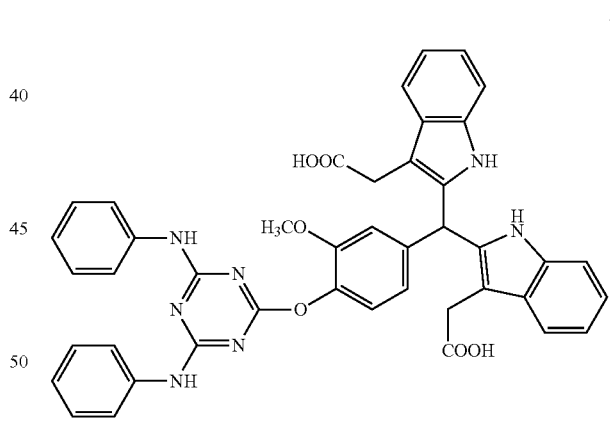

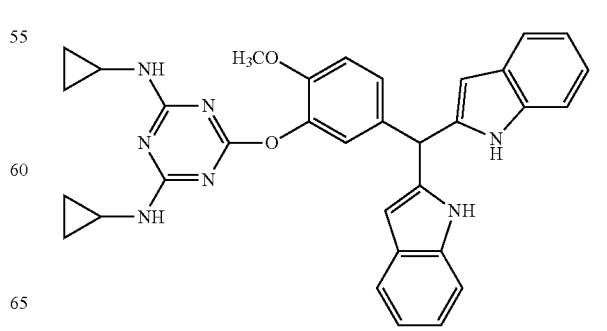

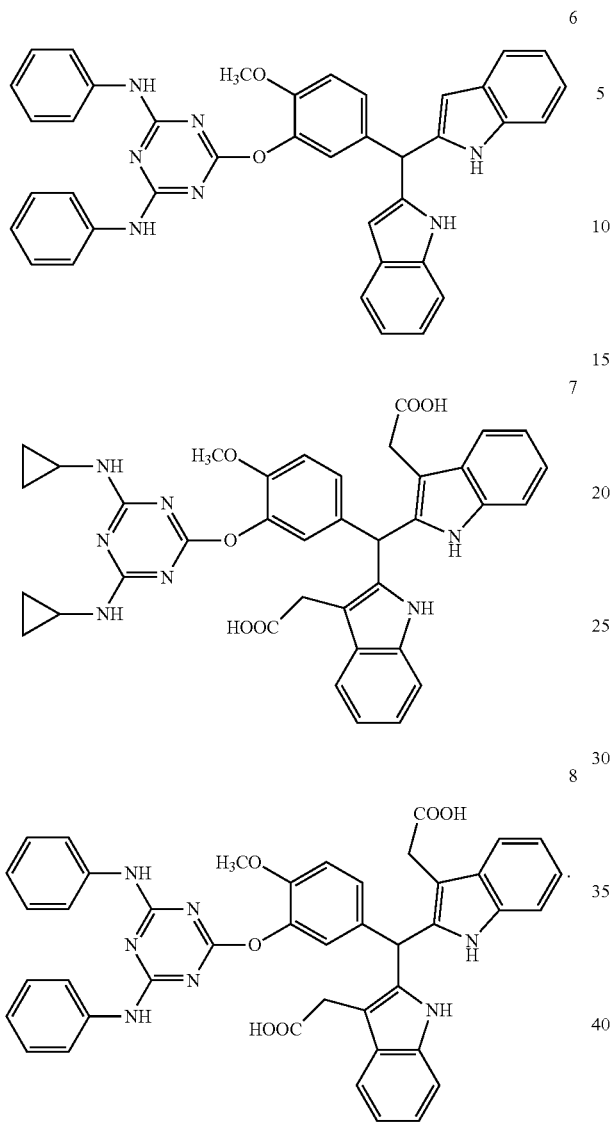

2. The triazine-aryl-bis-indole compound of claim 1, for the treatment of bronchial asthma comprising oral, mucosal or any other administration to a subject in need, said compound administered at a dose of about 1-20 μg/ml.

3. The triazine-aryl-bis-indole compound of claim 2, wherein the compound inhibits PDE 4 activity in vitro and thereby shows inhibition of PDE-4 enzyme up to 73% taking rolipram as standard.

4. A process for preparation of a triazine-aryl-bis-indole compound of claim 1 wherein the process steps comprise:
   a. reacting 2,4,6-trichloro-1,3,5-triazine (compound 9) with an amine in presence of a base at a temperature ranging between 0 to 40° C. for a period ranging between 1 to 2 hr to give the disubstituted chloro 1,3,5-triazine of formula A as shown below:

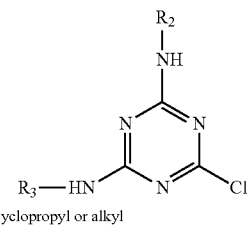

R2/R3 = Aryl or cyclopropyl or alkyl b. reacting the above disubstituted chloro 1,3,5-triazine with aromatic aldehyde in presence of a base at a temperature ranging between 50 to 70° C. for a period ranging between 4 to 6 hr to give the aryl ether of formula B as shown below:

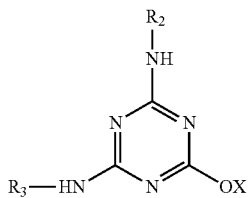

R2/R3 = Aryl or cyclopropyl or alkyl

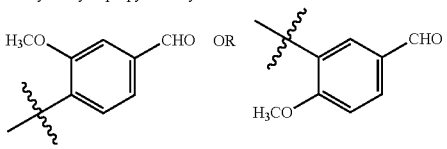

reacting the triazine-aryl ethers with indole or indole-3-acetic acid in the presence of an acid at a temperature ranging between 50 to 60° C. for a period ranging between 6 to 8 hr to give the triazine-aryl-bis-indole of claim 1.

5. The process for preparation of triazine-aryl-bis-indole compound of claim 4 wherein the amine is selected from an aliphatic amine or an aromatic amine.

6. The process for preparation of triazine-aryl-bis-indole compound of claim 4, wherein the aromatic aldehydes is selected from vaniline or isovaniline.

7. A pharmaceutical composition comprising one or more Triazine-aryl-bis-indole compounds of claim 1 along with the pharmaceutically acceptable additives, carriers or diluents.

8. Method of treatment of bronchial asthma comprising administering one or more Triazine-aryl-bis-indole compounds of claim 1 by oral, mucosal and any other route to a subject in need at a dose ranging between 0.1 to 1 mg/kg BW.

9. The process of claim 5 wherein the aliphatic amine is cyclopropyl amine.

10. The process of claim 5 wherein the aromatic amine is aniline.

11. Method of treatment of bronchial asthma comprising administering to a subject in need by oral, mucosal, or any other route a Triazine-aryl-bis-indole compound of claim 1 at a concentration ranging from 10 μg/mL to 20 μg/mL, thereby showing PDE4 inhibition ranging from 16-73%.

* * * * *